US011391745B2

(12) United States Patent
Kuroda et al.

(10) Patent No.: US 11,391,745 B2
(45) Date of Patent: Jul. 19, 2022

(54) METHOD OF DETECTING ARTERIOSCLEROSIS

(71) Applicants: FUJIKURA KASEI CO., LTD., Toyko (JP); National University Corporation Chiba University, Chiba (JP)

(72) Inventors: Hideyuki Kuroda, Kuki (JP); Rika Nakamura, Kuki (JP); Go Tomiyoshi, Kuki (JP); Takaki Hiwasa, Chiba (JP)

(73) Assignees: FUJIKURA KASEI CO., LTD., Tokyo (JP); National University Corporation Chiba University, Chiba (JP)

( * ) Notice: Subject to any disclaimer, the term of this patent is extended or adjusted under 35 U.S.C. 154(b) by 440 days.

(21) Appl. No.: 16/349,842

(22) PCT Filed: Nov. 10, 2017

(86) PCT No.: PCT/JP2017/040538
§ 371 (c)(1),
(2) Date: May 14, 2019

(87) PCT Pub. No.: WO2018/092684
PCT Pub. Date: May 24, 2018

(65) Prior Publication Data
US 2019/0277860 A1    Sep. 12, 2019

(30) Foreign Application Priority Data
Nov. 15, 2016    (JP) .............................. JP2016-222657

(51) Int. Cl.
*G01N 33/68*    (2006.01)
*G01N 33/564*    (2006.01)
(52) U.S. Cl.
CPC ....... *G01N 33/6893* (2013.01); *G01N 33/564* (2013.01); *G01N 2333/46* (2013.01); *G01N 2333/4703* (2013.01); *G01N 2800/323* (2013.01); *G01N 2800/56* (2013.01)
(58) Field of Classification Search
None
See application file for complete search history.

(56) References Cited

U.S. PATENT DOCUMENTS 6,596,476 B1 * 7/2003 Lesniewski .......... C07K 14/005
435/5
2013/0273579 A1   10/2013 Sawasaki et al.

OTHER PUBLICATIONS

Matsushita et al., Identification and Characterization of a Novel SH3-Domain Binding Protein, Sab, which preferentially Associates with Bruton's Tyrosine Kinase (Btk), Biochemical and Biophysical Research Communications, 245, (1998), p. 337-343 (Year: 1998).*

Harlow, E. and Lane, D., Antibodies: A Laboratory Manual (1988) Cold Spring Harbor Laboratory Press, Cold Spring Harbor, NY, p. 313 (Year: 1988).*
UniProtKB O60239, Accessed at: https://www.uniprot.org/uniprot/O60239 [Accessed Jul. 16, 2021, first available 1998] (13 pages) (Year: 1998).*
Harlow, E. and Lane, D., Antibodies: A Laboratory Manual (1988) Cold Spring Harbor Laboratory Press, Cold Spring Harbor, NY, pp. 23-26 (Year: 1988).*
Lederman et al., "A single amino acid substitution in a common African allele of the CD4 molecule ablates binding of the monoclonal antibody, OKT4" Mol Immunol. Nov. 1991;28(11):1171-81 (Year: 1991).*
Colman et al., Effects of amino acid sequence changes on antibody-antigen interactions, Research in Immunology, 1994; 145(1): 33-36 (Year: 1994).*
Lohse et al., Autoimmune hepatitis, Journal of Hepatology, 55, (2011), p. 171-182 (Year: 2011).*
International Search Report dated Feb. 13, 2018-from the International Bureau in counterpart International application No. PCT/JP2017/040538, (5 pages).
International Preliminary Report on Patentability and Translation of Written Opinion, dated May 21, 2019 from the International Bureau in counterpart International application No. PCT/JP201 7/040538, (11 pages).
Hiwasa, T., "[2W4-p-1] Identification of Serum Antibody Markers Associated with Arteriosclerosis-Related Diseases", Annual Meeting of the Japanese Biochemical Society, 88th edition, 2015, 2 pages.
Hiwasa, T., et al.," Using Peptide Array to Screen Atherosclerosis Markers", Japan Society for Proteases in Pathophysiology, 20th ed., 2015, 4 pages.
Rollins, K., et al., "Systematic review of the impact of HbA1c on outcomes following surgery in patients with diabetes mellitus", Clinical Nutrition, vol. 35, 2016, pp. 308-316.
Nakanishi, N., et al., "Cardiovascular Diseases: Serum uric acid and risk for development of hypertension and impaired fasting glucose or Type II diabetes in Japanese male office workers", European Journal of Epidemiology, vol. 18, 2003, pp. 523-530 (8 pages).
Liang, K., et al.,"Autoantibodies and the Risk of Cardiovascular Events", J. Rheumatol., vol. 36, No. 11, 2009, 2462-2469 (pp. 1-17 in manuscript).
Montecucco, F., et al., "Anti-Apolipoprotein A-1 auto-antibodies are active mediators of atherosclerotic plaque vulnerability", European Heart Journal, vol. 32, 2011, pp. 412-421.

(Continued)

Primary Examiner — Ellen J Marcsisin
(74) Attorney, Agent, or Firm — Sughrue Mion, PLLC

(57) ABSTRACT

Objects of the present invention are to find a marker by which progression of arteriosclerosis can be directly grasped, to thereby provide motivation for prevention or treatment of arteriosclerosis itself, and to provide means for accurately grasping condition of arteriosclerosis-related disease including arteriosclerotic disease. The invention provides a method for acquiring data on progression of arteriosclerosis, the method including determining a level of an antibody against SH3BP5 protein or a part thereof in a body fluid sample collected from a biological body, and a data acquisition kit for performing the data acquisition method.

5 Claims, 7 Drawing Sheets
Specification includes a Sequence Listing.

(56) References Cited

OTHER PUBLICATIONS

Fesmire, J., et al., "Effects of autoimmune antibodies anti-LPL, anti-LDL and anti-OXLDL on lipid metabolism and atherosclerosis in systemic lupus erythematosus", Rev Bras Reumatol., vol. 50, No. 5, 2010, 539-551 (pp. 1-14 in manuscript).

Carbone, F., et al.. "Evidence on the pathogenic role of autoantibodies in acute cardiovascular disease", Thrombosis and Haemostasis, vol. 109, 2013, pp. 854-868 (16 pages).

Kramer, J., et al., "Frequencies of Certain Complement Protein Alleles and Serum Levels of Anti-Heat-Shock Protein Antibodies in Cerebrovascular Diseases", Stroke, vol. 31, 2000, pp. 2648-2652.

Palmer, J.P., et al., "Insulin Antibodies in Insulin-Dependent Diabetics Before Insulin Treatment", Science, vol. 222, 1983, pp. 1337-1339 (4 pages).

Baekkeskov, S., et al., "Identification of the 64K autoantigen in insulin-dependent diabetes as the GABA-synthesizing enzyme glutamic acid decarboxylase", Nature, vol. 347, 1990, pp. 151-156.

Payton, M., et al., " Relationship of the 37,000- and 40,000-$M_r$ Tryptic Fragments of Islet Antigens in Insulin-dependent Diabetes to the Protein Tyrosine Phosphatase-like Molecule IA-2 (ICA512)", J. Clin. Invest., vol. 96, 1995, pp. 1506-1511.

Taplin, C., et al.. "Autoantibodies in type 1 diabetes", Autoimmunity, vol. 41, No. 1, 2008, pp. 11-18 (9 pages).

Matsushita, M., et al., "Identification and Characterization of a Novel SH3-Domain Binding Protein, Sab, Which Preferentially Associates with Bruton's Tyrosine Kinase (Btk)", Biochemical and Biophysical Research Communications, vol. 245, No. 2,1998, pp. 337-343.

Yamadori, T., et al., "Bruton's tyrosine kinase activity is negatively regulated by Sab, the Btk-SH3 domain-binding protein", Proc. Natl. Acad. Sci. USA, Immunology, vol. 96, 1999, pp. 6341-6346.

Win, S., et al., "Sab (Sh3bp5) dependence of JNK mediated inhibition of mitochondrial respiration in palmitic acid induced hepatocyte lipotoxicity", J. Hepatol., vol. 62, No. 6, 2015, 1367-1374 (pp. 1-20 in manuscript).

Nakamura et al., "An Anti-Deoxyhypusine Synthase Antibody as a Marker of Atherosclerosis-Related Cerebral Infarction, Myocardial Infarction, Diabetes Mellitus, and Chronic Kidney Disease", SM Atherosclerosis Journal, vol. 1, No. 1, 2017, pp. 1-9.

Hiwasa et al., "Serum SH3BP5-specific Antibody Level is a Biomarker of Atherosclerosis", Immunome Research, vol. 13, Issue 2, 2017, pp. 1-11.

Santos et al., "Low Titers of Human Antioxidized LDL Autoantibodies are Associated with Unstable Coronary Disease", L015, Atherosclerosis Suppl., vol. 8, No. 3, 2007, pp. 20-21.

Bodolay et al., "Increased levels of anti-heat-shock protein 60 (anti-Hsp60) indicate endothelial dysfunction, atherosclerosis and cardiovascular diseases in patients with mixed connective tissue disease", Immunol Res., vol. 60, 2014, pp. 50-59.

Roux-Lombard et al., "Auto-antibodies as Emergent Prognostic Markers and Possible Mediators of Ischemic Cardiovascular Diseases", Clinic Rev Allerg Immunol, vol. 44, 2013, pp. 84-97.

Communication dated Aug. 31, 2020 by the European Patent Office in application No. 17871947.2, (10 pages).

* cited by examiner

[Fig. 1]
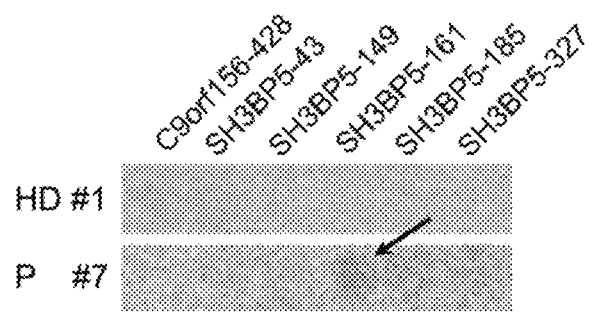

[Fig. 2]
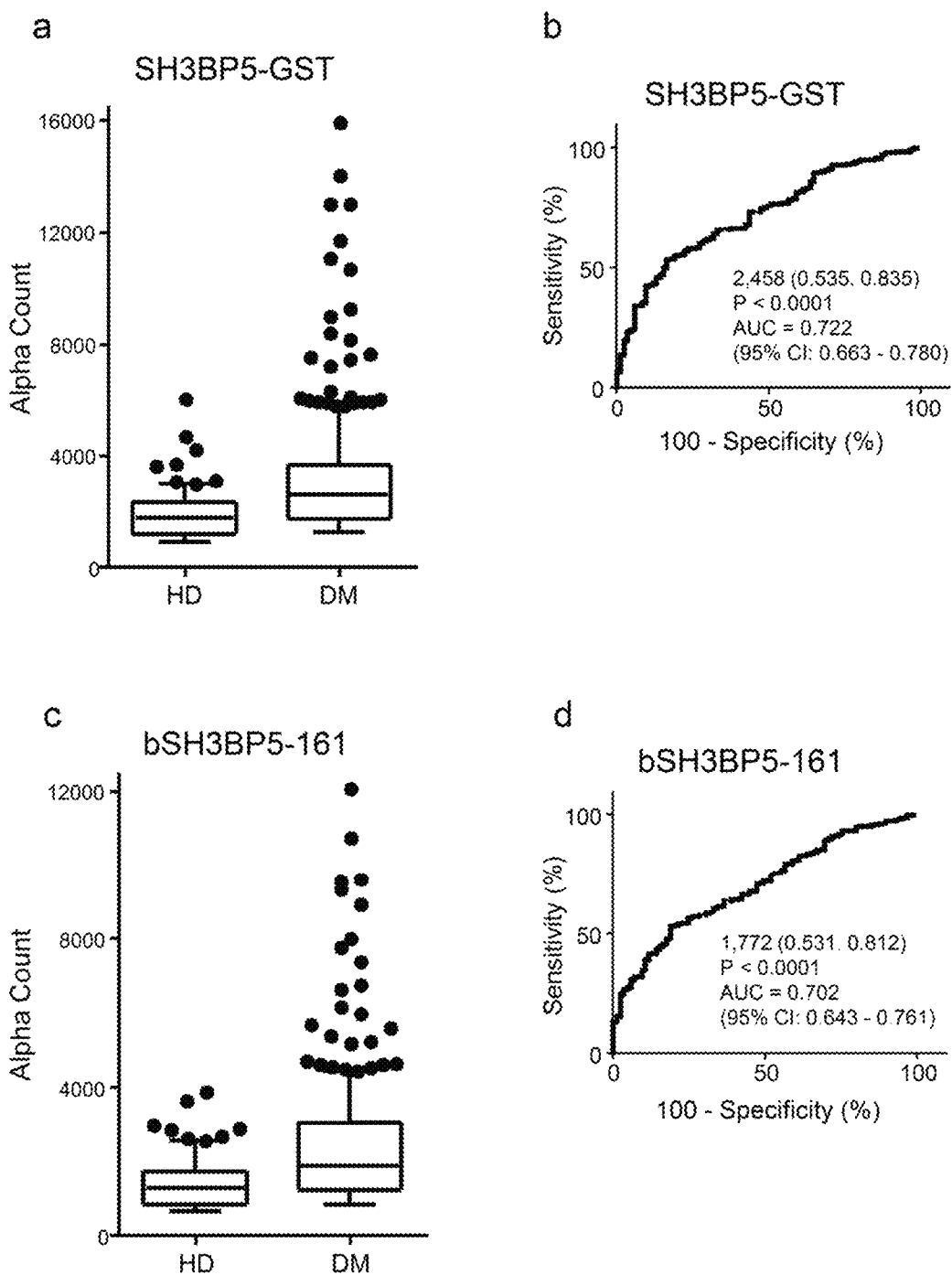

[Fig. 3-1]
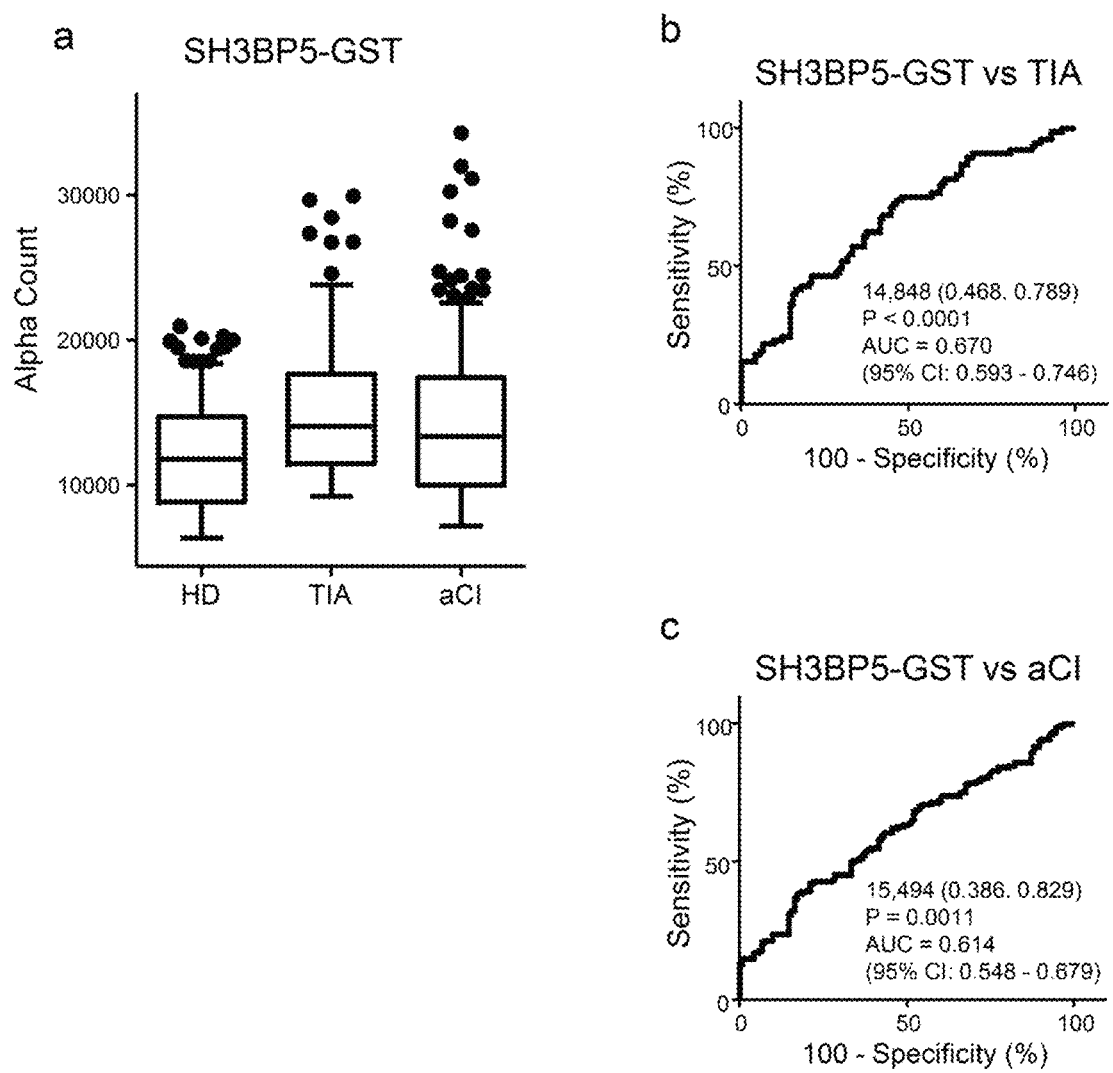

[Fig. 3-2]
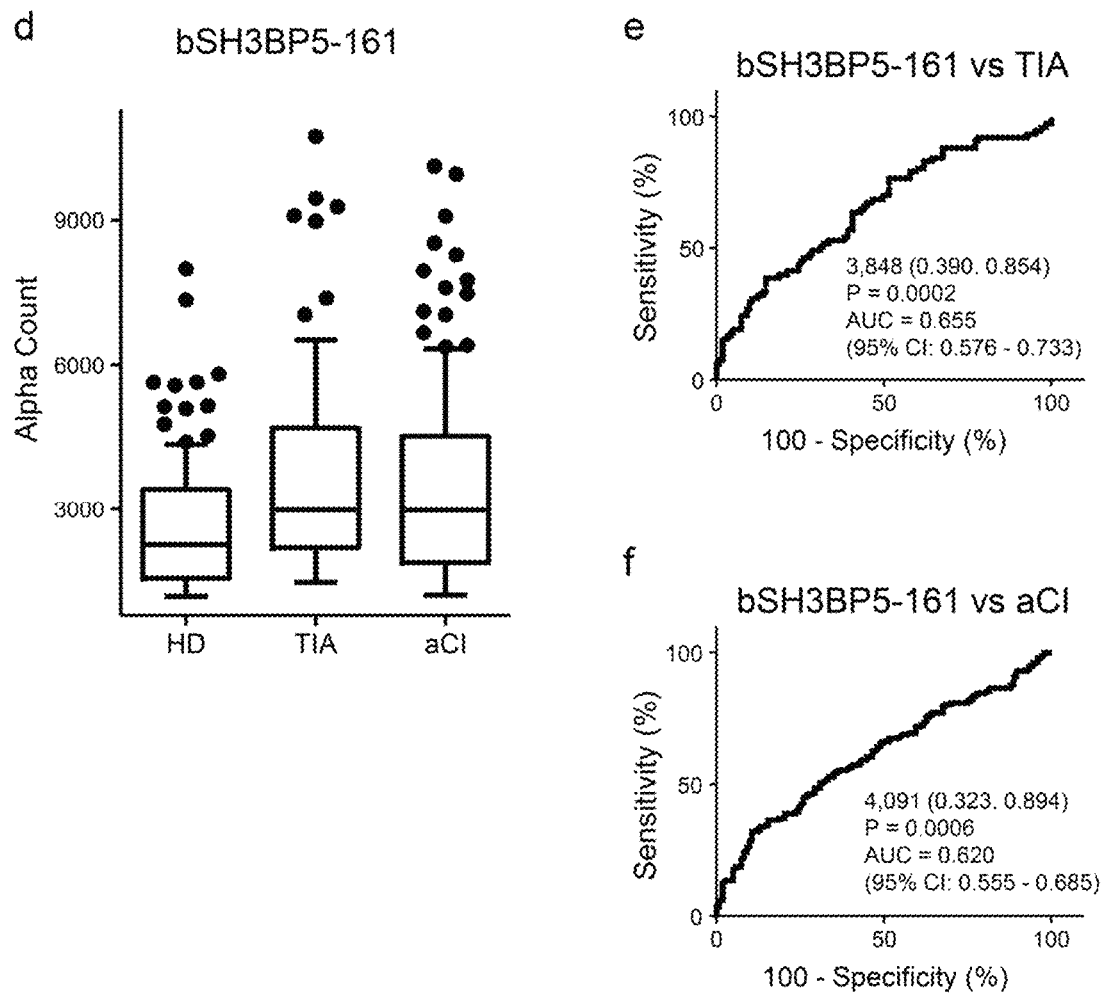

[Fig. 4]
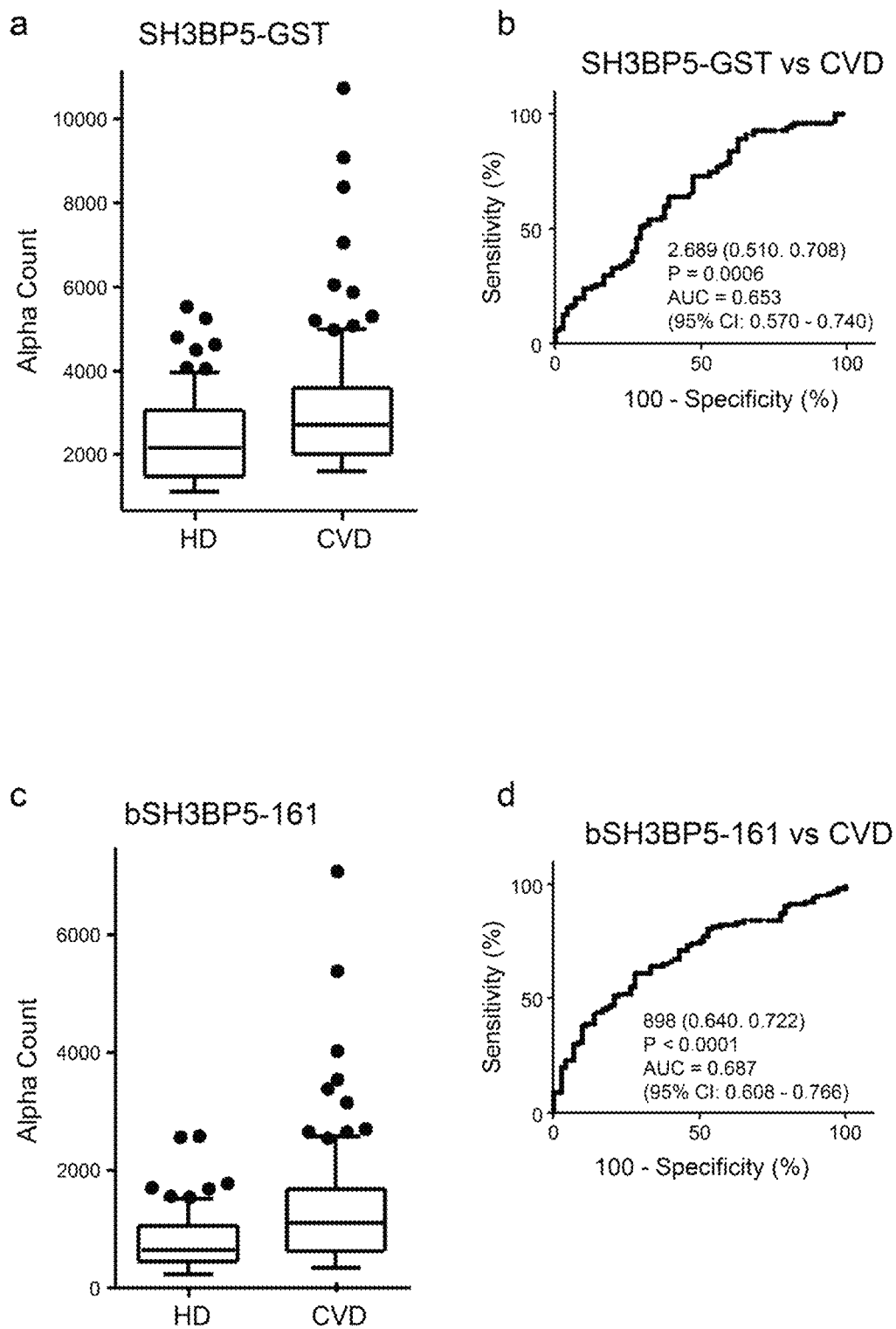

[Fig. 5-1]
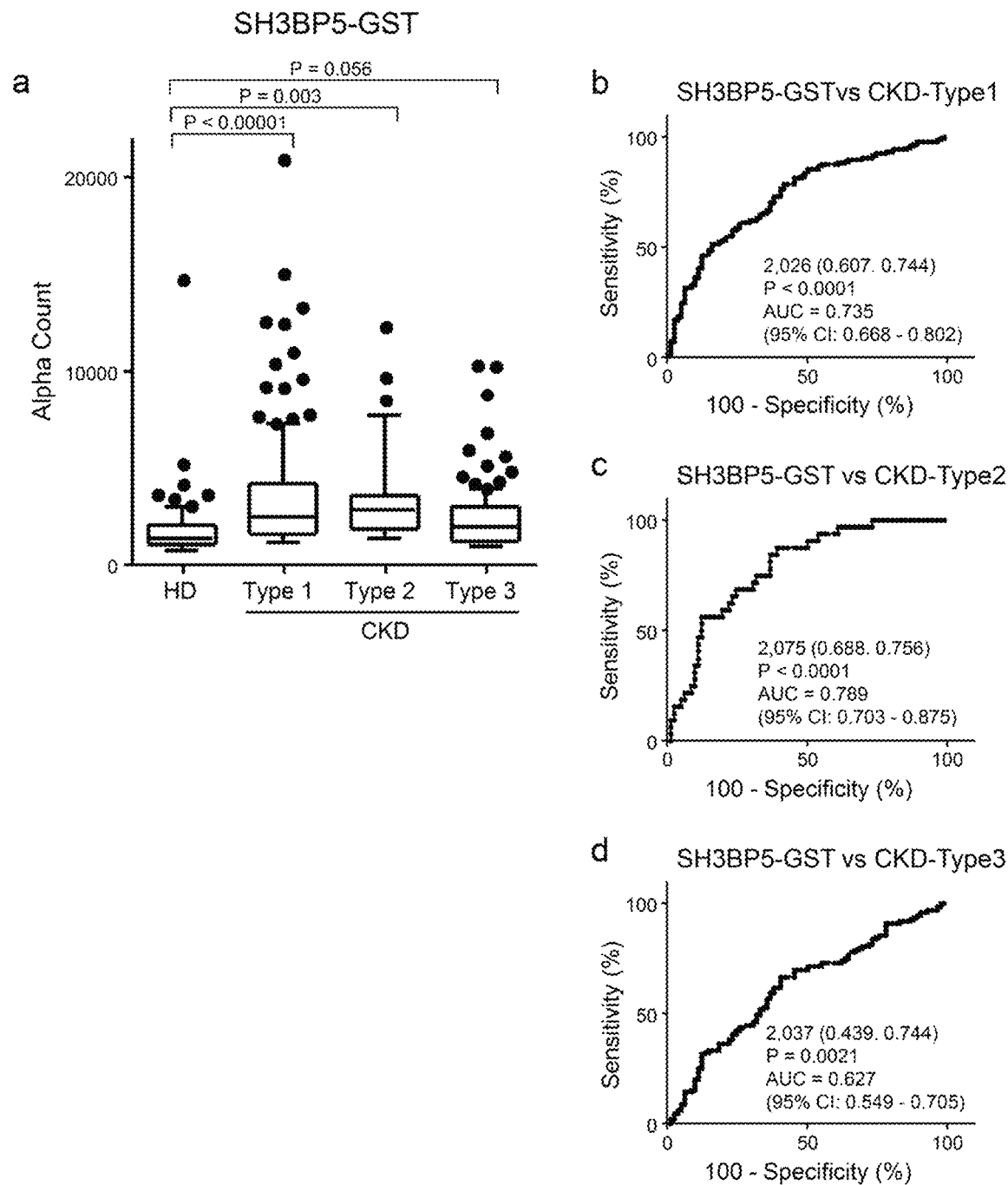

[Fig. 5-2]
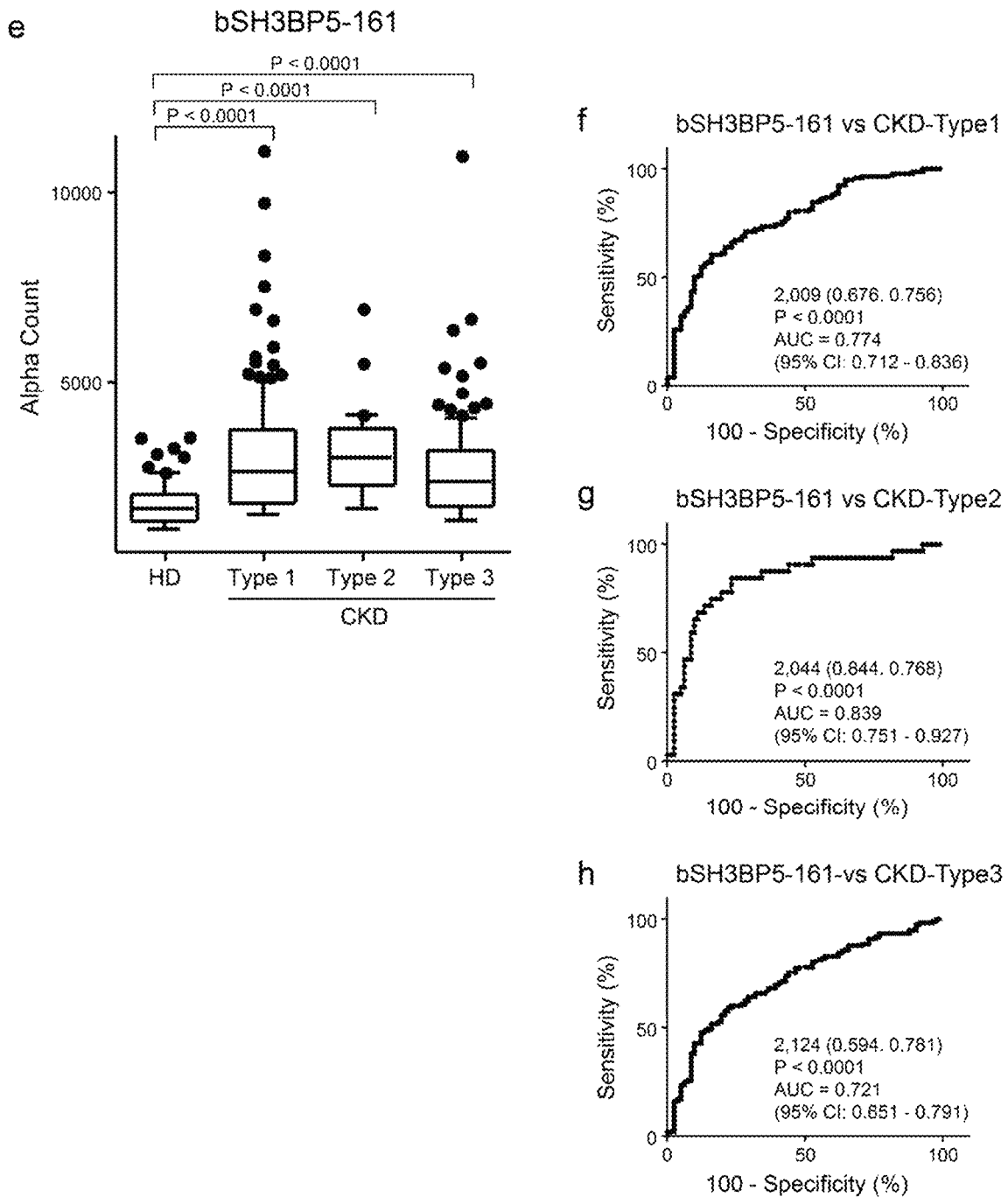

US 11,391,745 B2

METHOD OF DETECTING ARTERIOSCLEROSIS

CROSS REFERENCE TO RELATED APPLICATIONS

This application is a National Stage of International Application No. PCT/JP2017/040538, filed on Nov. 10, 2017, which claims priority from Japanese Patent Application No. 2016-222657, filed on Nov. 15, 2016.

TECHNICAL FIELD

The present invention relates to means for detecting disease. More particularly, the present invention relates to means for grasping progression of arteriosclerosis through detection of an antibody against SH3BP5 protein in a body fluid (e.g., blood). The present invention also enables detection of arteriosclerosis-related disease.

BACKGROUND ART

Arteriosclerosis is a generic pathological term for a "lesion associated with breakage of the original structure of the artery and dysfunction thereof caused by thickening and/or hardening of the arterial wall," and arteriosclerosis often progresses asymptomatically. Atherosclerosis, which is the most typical type of arteriosclerosis, is likely to occur in the coronary artery (artery supplying blood to the heart), the aorta, and the arteries of the brain, the cervix, the kidneys, the viscera, or the limbs. Atherosclerosis involves accumulation of cholesterol in the intima of the arterial wall, gradual deposition of lipids therein, narrowing of the blood vessel, and facilitation of thrombus formation or ulceration. These cause arteriosclerotic disease, such as angina, myocardial infarction, cerebral infarction, cerebral hemorrhage, aortic aneurysm, nephrosclerosis, arteriosclerosis obliterans, and necrotic limbs.

Arteriosclerotic disease, such as cerebral infarction and myocardial infarction, generally leads directly to death. Even if the disease does not lead to death, it requires long-term rehabilitation of the patient. The disease places a heavy burden on the patient and patient's family, leading to an increase in national medical expenses from a social perspective. Thus, prevention of the onset of the disease is an important issue. If progression of arteriosclerosis can be grasped to thereby predict the subsequent onset of cerebral infarction or myocardial infarction, arteriosclerotic disease as a whole is highly likely to be prevented by treatment before the onset of the disease and/or improvement in lifestyle.

Therefore, in order to grasp condition of arteriosclerotic disease, blood tests have generally been performed for determining, for example, high-density lipoprotein (HDL) cholesterol, low-density lipoprotein (LDL)-cholesterol, total cholesterol (TC), glycohemoglobin (HbA1c) (Non-Patent Document 1), and uric acid (Non-Patent Document 2).

In addition, as blood antibody markers, phospholipid (Non-Patent Document 3), apolipoprotein A-1 (Non-Patent Document 4), oxidized low-density lipoprotein (Non-Patent Document 5), and heat shock proteins (Hsps) (Non-Patent Document 6) for cardiovascular disease; Hsp60 (Non-Patent Document 7) for cerebral stroke; insulin (Non-Patent Document 8), glutamic acid decarboxylase (GAD) (Non-Patent Document 9), and protein tyrosine phosphatase IA-2 (Non-Patent Documents 10 and 11) for diabetes mellitus, etc. are known.

PRIOR ART DOCUMENTS

Non-Patent Documents

Non-Patent Document 1: Rollins KE, Varadhan KK, Dhatariya K, Lobo DN (2015) Systematic review of the impact of HbA1c on outcomes following surgery in patients with diabetes mellitus. Clin Nutr S0261-5614: 00082-5.

Non-Patent Document 2: Nakanishi N, Okamoto M, Yoshida H, Matsuo Y, Suzuki K, et al. (2003) Serum uric acid and risk for development of hypertension and impaired fasting glucose or type II diabetes in Japanese male office workers. Eur J Epidemiol 18: 523-530.

Non-Patent Document 3: Liang, K. P., Kremers, H. M., Crowson, C. S., Snyder, M. R., Therneau, T. M., Roger, V. L. and Gabriel, S. E. Autoantibodies and the risk of cardiovascular events. J. Rheumatol., 2009, 36, 2462-2469.

Non-Patent Document 4: Montecucco, F., Vuilleumier, N., Pagano, S., Lenglet, S., Bertolotto, M., Braunersreuther, V., Pelli, G., Kovari, E., Pane, B., Spinella, G., Pende, A., Palombo, D., Dallegri, F., Mach, F. and Roux-Lombard, P. Anti-apolipoprotein A-1 auto-antibodies are active mediators of atherosclerotic plaque vulnerability. Eur. Heart J., 2011, 32, 412-421.

Non-Patent Document 5: Fesmire, J., Wolfson-Reichlin, M. and Reichlin, M. Effects of autoimmune antibodies antilipoprotein lipase, anti-low density lipoprotein, and anti-oxidized low density lipoprotein on lipid metabolism and atherosclerosis in systemic lupus erythematosus. Rev. Bras. Reumatol., 2010, 50, 539-551.

Non-Patent Document 6: Carbone, F., Nencioni, A., Mach, F., Vuilleumier, N. and Montecucco, F. Evidence on the pathogenic role of auto-antibodies in acute cardiovascular diseases. Thromb. Haemost., 2013, 109, 854-868.

Non-Patent Document 7: Kramer, J., Harcos, P., Prohaszka, Z., Horvath, L., Karadi, I., Singh, M., Csaszar, A., Romics, L. and Fust, G. Frequencies of certain complement protein alleles and serum levels of anti-heat-shock protein antibodies in cerebrovascular diseases. Stroke, 2000, 31, 2648-2652.

Non-Patent Document 8: Palmer, J. P., Asplin, C. M., Clemons, P., Lyen, K., Tatpati, O., Raghu, P. K. and Paquette, T. L. Insulin antibodies in insulin-dependent diabetics before insulin treatment. Science, 1983, 222, 1337-1339.

Non-Patent Document 9: Baekkeskov, S., Aanstoot, H., Christgau, S., Reetz, A., Solimena, M. S., Cascalho, M., Folli, F., Richter-Olsen, H. and DeCamilli, P. Identification of the 64K autoantigen in insulin dependent diabetes as the GABA-synthesizing enzyme glutamic acid decarboxylase. Nature, 1990, 347, 151-156.

Non-Patent Document 10: Payton, M. A., Hawkes, C. J. and Christie, M. R. Relationship of the 37,000- and 40,000-M(r) tryptic fragments of islet antigens in insulin-dependent diabetes to the protein tyrosine phosphatase-like molecule IA-2 (ICA512). J. Clin. Invest., 1995, 96, 1506-1511.

Non-Patent Document 11: Taplin, C. E. and Barker, J. M. Autoantibodies in type 1 diabetes. Autoimmunity, 2008, 41, 11-18.

Non-Patent Document 12: Matsushita, M., Yamadori, T., Kato, S., Takemoto, Y., Inazawa, J., Baba, Y., Hashimoto, S., Sekine, S., Arai, S., Kunikata, T., Kurimoto, M., Kishimoto, T., Tsukada, S. Identification and characterization of a novel SH3-domain binding protein, Sab, which preferentially associates with Bruton's tyrosine kinase (Btk). Biochem. Biophys. Res. Commun., 1998, 245, 337-343.

Non-Patent Document 13: Yamadori, T., Baba, Y., Matsushita, M., Hashimoto, S., Kurosaki, M., Kurosaki, T., Kishimoto, T. and Tsukada, S. Bruton's tyrosine kinase activity is negatively regulated by Sab, the Btk-SH3 domain-binding protein. Proc. Nat. Acad. Sci. USA, 1999, 96, 6341-6346.

Non-Patent Document 14: Win, S., Than, T. A., Le, B. H., Garcia-Ruiz, C., Fernandez-Checa, J. C. and Kaplowitz, N. Sab (Sh3bp5) dependence of JNK mediated inhibition of mitochondrial respiration in palmitic acid induced hepatocyte lipotoxicity. J. Hepatol., 2015, 62(6), 1367-1374.

DISCLOSURE OF THE INVENTION

Problems to be Solved by the Invention

As described above, attempts have been made to grasp condition of arteriosclerotic disease by use of various markers. Such an attempt to grasp the condition using markers is from the side of risk factors of arteriosclerotic disease; i.e., an indirect mode of grasping the condition. In such a mode of grasping the condition, the condition of arteriosclerotic disease can be grasped on the basis of the given risk factors. However, the markers do not necessarily correspond to all risk factors of arteriosclerotic disease, and thus may lead to oversight of progression of arteriosclerosis itself.

An object of the present invention is to find a marker by which progression of arteriosclerosis can be directly grasped, to thereby provide motivation for prevention or treatment of arteriosclerosis itself. Another object of the present invention is to provide means for accurately grasping condition of arteriosclerosis-related disease including arteriosclerotic disease.

Means for Solving the Problems

The present inventors have found that progression of arteriosclerosis can be accurately grasped through determination of the level of an antibody against SH3BP5 protein in a body fluid. The present invention has been accomplished on the basis of this finding.

The term "arteriosclerosis" as used herein refers to a "lesion associated with breakage of the original structure of the artery and dysfunction thereof caused by thickening and/or hardening of the arterial wall." The term "arteriosclerosis-related disease" as used herein refers to "disease relating to arteriosclerosis" and includes both "disease caused by arteriosclerosis" and "disease causing arteriosclerosis." The term "arteriosclerotic disease" as used herein refers to "disease caused by arteriosclerosis" as mentioned above and is a subordinate concept of the arteriosclerosis-related disease.

In a first aspect of the present invention, there is provided a method for acquiring data on progression of arteriosclerosis, the method being characterized by comprising determining the level of an antibody against SH3BP5 protein or a part thereof in a body fluid sample collected from a biological body (hereinafter the method may be referred to as "the data acquisition method of the present invention").

SH3BP5 protein, serving as an antigen, is an essential for capturing a body fluid antibody that is an assay target in the data acquisition method of the present invention. SH3BP5 protein is also called SH3 domain-binding protein 5 or Sab and is registered in NCBI (Accession No. NM_004844). SH3BP5 protein was discovered as a protein that binds to Bruton tyrosine kinase (BTK) and inhibits activity of BTK (Non-Patent Documents 12 and 13). SH3BP5 protein is known to induce lipid toxicity or non-alcoholic steatohepatitis (NASH) together with c-Jun N-terminal kinase (JNK) (Non-Patent Document 14).

The gene encoding SH3BP5 protein (SH3BP5 gene) has a nucleotide sequence as shown in SEQ ID NO: 1 (nucleotide sequence), and the protein has an amino acid sequence as shown in SEQ ID NO: 2 (amino acid sequence).

The data acquisition method of the present invention can also be represented by, for example, "a method for grasping progression of arteriosclerosis, the method being characterized by comprising determining the level of an antibody against SH3BP5 protein or a part thereof in a body fluid sample collected from a biological body."

A second aspect of the present invention provides a data acquisition kit for carrying out the data acquisition method of the present invention (hereinafter the kit may be referred to as "the kit of the present invention").

The data acquisition kit of the present invention can also be represented by, for example, "a kit for carrying out a method for grasping progression of arteriosclerosis, the method being characterized by comprising determining the level of an antibody against SH3BP5 protein or a part thereof in a body fluid sample collected from a biological body."

Effects of the Invention

The present invention provides means for directly grasping progression of arteriosclerosis by use of a body fluid antibody marker. Thus, there is provided motivation for prevention or treatment of arteriosclerosis itself, as well as means for accurately grasping condition of the arteriosclerosis-related disease including arteriosclerotic disease. The present invention also enables detection of an individual arteriosclerosis-related disease.

BRIEF DESCRIPTION OF THE DRAWINGS

FIG. 1 shows the results of a body fluid antibody-capturing assay performed on an array with peptides derived from SH3BP5 protein.

FIG. 2 shows the results of comparison of the level of anti-SH3BP5 antibody in sera from diabetes (DM) patients and healthy subjects (HD) by ALPHALISA®. FIG. 2 consists of four drawings (FIGS. 2a to 2d). FIG. 2a is a boxplot showing the results in the case of use of SH3BP5 protein antigen, and FIG. 2c is a boxplot showing the results in the case of use of SH3BP5 peptide antigen. The vertical axis of each of these boxplots corresponds to Alpha Count, and the borders shown in each boxplot correspond to (from bottom to top) 10th percentile (the lowermost horizontal bar), 20th percentile (the bottom line of the box), 50th percentile (the center line of the box), 80th percentile (the top line of the box), and 90th percentile (the uppermost horizontal bar). FIGS. 2b and 2d are ROC curves reflecting the results shown in FIGS. 2a and 2c, respectively. Numerical values in the four rows shown in each of the ROC curves of FIGS. 2b and 2d correspond to (from top to bottom) cutoff value (sensitivity and specificity), P value, areas under the curve (AUC) value, and 95% CI.

FIG. 3 shows the results of comparison of the level of serum anti-SH3BP5 antibody in transient ischemic attack (TIA) patients, acute-stage cerebral infarction (aCI) patients, and healthy subjects by ALPHALISA®. FIG. 3 consists of six drawings (FIGS. 3a to 3f), and FIG. 3-1 consists of three drawings (FIGS. 3a to 3c). FIG. 3a is a boxplot showing the results in the case of use of SH3BP5 protein as a body fluid antibody-capturing antigen; FIG. 3b is an ROC curve corresponding to the results of TIA shown in FIG. 3a; and FIG. 3c is an ROC curve corresponding to the results of aCI shown in FIG. 3a. Numerical values in the four rows shown in each ROC curve have the same meanings as defined above in, for example, FIG. 2b.

FIG. 3-2 consists of three drawings (FIGS. 3d to 3f) showing the results in the case of use of SH3BP5 peptide as an antibody-capturing antigen. FIG. 3d is a boxplot showing the results in the case of use of SH3BP5 peptide; FIG. 3e is an ROC curve corresponding to the results of TIA shown in FIG. 3d; and FIG. 3f is an ROC curve corresponding to the results of aCI shown in FIG. 3d. Numerical values in the four rows shown in each ROC curve have the same meanings as defined above in, for example, FIG. 2b.

FIG. 4 shows the results of comparison of the level of serum anti-SH3BP5 antibody in healthy subjects and cardiovascular disease patients. FIG. 4 consists of four drawings (FIGS. 4a to 4d). FIG. 4a is a boxplot showing the results in the case of use of SH3BP5 protein antigen, and FIG. 4c is a boxplot showing the results in the case of use of SH3BP5 peptide antigen. FIGS. 4b and 4d are ROC curves reflecting the results shown in FIGS. 4a and 4c, respectively. Numerical values in the four rows shown in each ROC curve have the same meanings as defined above in, for example, FIG. 2b.

FIG. 5 shows the results of comparison of the level of serum anti-SH3BP5 antibody in healthy subjects and chronic kidney disease (CKD) patients by ALPHALISA®. FIG. 5 consists of eight drawings (FIGS. 5a to 5h), and FIG. 5-1 consists of four drawings (FIGS. 5a to 5d). FIG. 5a is a boxplot showing the results in the case of use of SH3BP5 protein as a body fluid antibody-capturing antigen; FIG. 5b is an ROC curve corresponding to the results of Type 1 shown in FIG. 5a; FIG. 5c is an ROC curve corresponding to the results of Type 2 shown in FIG. 5a; and FIG. 5d is an ROC curve corresponding to the results of Type 3 shown in FIG. 5a. Numerical values in the four rows shown in each ROC curve have the same meanings as defined above in, for example, FIG. 2b.

FIG. 5 shows the results of comparison of the level of serum anti-SH3BP5 antibody in healthy subjects and chronic kidney disease (CKD) patients by ALPHALISA®. FIG. 5 consists of eight drawings (FIGS. 5a to 5h), and FIG. 5-2 consists of four drawings (FIGS. 5e to 5h). FIG. 5e is a boxplot showing the results in the case of use of SH3BP5 peptide as a body fluid antibody-capturing antigen; FIG. 5f is an ROC curve corresponding to the results of Type 1 shown in FIG. 5e; FIG. 5g is an ROC curve corresponding to the results of Type 2 shown in FIG. 5e; and FIG. 5h is an ROC curve corresponding to the results of Type 3 shown in FIG. 5e. Numerical values in the four rows shown in each ROC curve have the same meanings as defined above in, for example, FIG. 2b.

MODES FOR CARRYING OUT THE INVENTION (1) The Data Acquisition Method of the Present Invention
(a) Body Fluid Sample Collected from Biological Body (Hereinafter the Sample May be Referred to Simply as "Body Fluid Sample" or "Sample")

The "body fluid sample collected from a biological body," which is used as a data acquisition target in the data acquisition method of the present invention, is a body fluid as is collected from the body, or a product prepared through any treatment of the body fluid. The "body fluid" may be, for example, blood or lymph. The body fluid sample is preferably a blood sample. The blood sample may be, for example, whole blood, serum, or plasma, and is preferably serum or plasma, particularly preferably serum. The blood sample may be subjected to an anticoagulation treatment such as heparin treatment. In the present invention, the detection target substance in the body fluid sample is an antibody against SH3BP5 (the antibody is referred to herein as "body fluid antibody," "autoantibody," or "body fluid autoantibody").

(b) Antigen for Capturing Body Fluid Antibody

SH3BP5 protein is an essential for capturing a body fluid antibody in the data acquisition method of the present invention. The entirety of the protein which has an amino acid sequence of SEQ ID NO: 2 may be used as an antigen for capturing a body fluid antibody (hereinafter may be referred to as a "body fluid antibody-capturing antigen"), or a part of the protein may be used as a body fluid antibody-capturing antigen. In the case where a part of the protein which has an amino acid sequence of SEQ ID NO: 2 is used as a body fluid antibody-capturing antigen, 7 to 455 consecutive amino acid residues in the amino acid sequence of SEQ ID NO: 2 can be selected as a body fluid antibody-capturing antigen. A peptide having a relatively short amino acid sequence may be selected for establishment of a more effective detection system. In such a case, the number of amino acid residues is preferably about 7 to about 30, more preferably about 10 to about 20.

In the entirety or a part of the amino acid sequence of SEQ ID NO: 2, the number (truncated to an integer) corresponding to 10% or less of the amino acid residues may be modified (deleted, substituted, or added). In such a case, the amino acid sequence is preferably modified to such an extent that the resultant protein or a part thereof can capture a target body fluid antibody.

The term "deletion" as used herein refers to deletion of any amino acid residue(s) in a target amino acid sequence, wherein the amino acid residue on the N-terminal side (forward) of the deleted amino acid residue(s) is bound via a peptide bond to the amino acid residue on the C-terminal side (backward) of the deleted amino acid residue(s) (note: deletion of an amino acid residue at the N-terminus or the C-terminus does not involve formation of a peptide bond). The number of deleted amino acid residues may also be referred to as "the number of amino acid deletions." The term "substitution" as used herein refers to substitution of any amino acid residue(s) in a target amino acid sequence by "another amino acid residue(s)," wherein the substituted amino acid residue(s) is bound via a peptide bond to each of the amino acid residues on the N-terminal side (forward) and the C-terminal side (backward) (substitution of an amino acid residue at the N-terminus involves formation of a peptide bond with only the amino acid residue on the C-terminal side, and substitution of an amino acid residue at the C-terminus involves formation of a peptide bond with only the amino acid residue on the N-terminal side). The number of substituted amino acid residues may also be referred to as "the number of amino acid substitutions." The term "addition" as used herein refers to the state where one or more new amino acid residues are inserted at any of one or more peptide bonds of amino acid residues in a target amino acid sequence, and new peptide bonds are formed.

The term "addition" includes addition of one or more new amino acid residues at the N-terminus or the C-terminus. The number of "added" amino acid residues may also be referred to as "the number of amino acid additions."

The phrase "can capture a target body fluid antibody" described above refers to the case where, when a body fluid antibody is captured with a body fluid antibody-capturing antigen candidate having a modified amino acid residue(s) by a technique similar to that described herein in the Examples, condition of a target arteriosclerotic disease can be grasped on the basis of the level of the captured antibody.

Specific examples of the amino acid sequence of a peptide used as a body fluid antibody-capturing antigen include SEQ ID NO: 3 (SH3BP5-43: FRSVLVEATVKLDE), SEQ ID NO: 4 (SH3BP5-149: VHKETAARYNAAMG), SEQ ID NO: 5 (SH3BP5-161: MGRMRQLEKKLKRA), SEQ ID NO: 6 (SH3BP5-185: KAKYYVQLEQLKKT), and SEQ ID NO: 7 (SH3BP5-327: EFGMMFPVLGPRSE). Among these peptides used as body fluid antibody-capturing antigens, the peptide having an amino acid sequence of SEQ ID NO: 5 is preferred. In any of these antibody-capturing peptides, only one amino acid residue can be modified in the amino acid sequence according to the above criteria.

A body fluid antibody-capturing antigen having a specific amino acid sequence may be obtained through a common technique. Specifically, such a body fluid antibody-capturing antigen may be prepared as follows. On the basis of, for example, the aforementioned nucleotide sequence of SEQ ID NO: 1, nucleotide amplification primers are designed for amplifying double-stranded DNA having the entirety or a part of the nucleotide sequence of SH3BP5 gene. A gene amplification product is prepared as the entirety or a part of SH3BP5 gene by means of, for example, PCR using the primers for amplification. The amplification product is incorporated into a prokaryotic cell expression vector (e.g., pGEX-4T). A transformant obtained through incorporation of the vector is selected, followed by addition of a chemical (e.g., IPTG (isopropyl-β-D-thiogalactoside)), to thereby induce expression of the entirety or a part of SH3BP5 gene. The entirety or a part of SH3BP5 protein produced through the gene expression can be purified by means of, for example, affinity chromatography using Glutathione-Sepharose (GE Healthcare Life Sciences). The nucleotide sequence of SH3BP5 gene may be subjected to deletion, substitution, or addition by a common technique, such as site-specific mutagenesis (Methods in Enzymology, 154, 350, 367-382 (1987); Methods in Enzymology, 100, 468 (1983); Nucleic Acids Res., 12, 9441 (1984)), to thereby produce SH3BP5 protein having the corresponding modification.

In particular, a peptide having a sequence corresponding to a part of SH3BP5 protein (typically, a peptide used as a body fluid antibody-capturing antigen having 7 to 30 amino acid residues as described above) can be readily produced through any known chemical peptide synthesis method. Specifically, the peptide can be produced by a solid-phase peptide synthesis method or a liquid-phase peptide synthesis method, which has been established as a customary method. Also, the peptide can be produced by the Boc solid-phase method or the Fmoc solid-phase method, which is a solid-phase peptide synthesis method generally recognized as a suitable chemical synthesis method.

SH3BP5 protein may be a commercially available product. The commercially available product includes a ready-made product and a product manufactured through outsourcing upon request Such a protein or peptide used as a body fluid antibody-capturing antigen (i.e., an essential material for capturing a body fluid antibody) may optionally be modified with an appropriate structure. For example, as described below, the protein or the peptide may be a GST (glutathione S-transferase)-fused protein or peptide, or a biotinylated protein or peptide, which is used in ALPHALISA® (amplified luminescence proximity homogeneous assay-linked immunosorbent assay).

(c) Method for Acquiring Data on Progression of Arteriosclerosis

The data acquisition method of the present invention involves determination of the level of a body fluid antibody against SH3BP5 protein or peptide in a body fluid sample (e.g., a blood sample). In the case where the thus-determined level is higher than a reference value, the level of SH3BP5 protein is considered as high in the body fluid sample provider. The results can be regarded as data on progression of arteriosclerosis in the test sample provider.

Examples of arteriosclerosis include atherosclerosis, arteriolosclerosis, and medial sclerosis.

The present invention achieves acquisition of direct data on progression of arteriosclerosis. Specifically, the presence of arteriosclerosis can be grasped even in the absence of specific symptoms in association with the progression of arteriosclerosis. The progression of arteriosclerosis can be prevented by taking measures for reducing risk factors (e.g., guidance for lifestyle modification, such as dietary guidance, exercise guidance, or antismoking guidance) at the stage where no symptoms of arteriosclerosis are observed. In the case where hyperlipidemia or hypertension is observed by another means, prescription of an appropriate drug, such as an anticholesterol agent, an antihypertensive agent, or an antithrombotic agent, can reduces progress of these risk factors of arteriosclerosis.

In the present invention, data on progression of arteriosclerosis may be data for detection of arteriosclerosis-related disease. Thus, data showing an increase in the level of SH3BP5 protein in a body fluid sample provider can be used as a direct index data on arteriosclerosis-related disease.

As described above, the term "arteriosclerosis-related disease" refers to "disease relating to arteriosclerosis" and includes both "disease caused by arteriosclerosis (arteriosclerotic disease)" and "disease causing arteriosclerosis." Examples of the disease causing arteriosclerosis include diabetes, chronic kidney disease, dyslipidemia, familial hypercholesterolemia, hypertension, non-cardiogenic cerebral infarction, peripheral arterial disease, and sleep apnea syndrome. Examples of the arteriosclerotic disease include cardiovascular disease such as angina and myocardial infarction, cerebral infarction, transient ischemic attack, cerebral hemorrhage, subarachnoid hemorrhage, aortic aneurysm, nephrosclerosis, arteriosclerosis obliterans, and necrotic limbs.

In the present invention, a mode in which data for detection of the aforementioned arteriosclerosis-related disease are data for detection of the aforementioned arteriosclerotic disease is particularly mentioned.

The reference value of the level of a body fluid antibody against SH3BP5 protein in a test sample can be obtained as follows. In a sample of subjects who are regarded as having no arteriosclerosis by means of a common clinical test, the level of a body fluid antibody against SH3BP5 protein in the test sample from each of the subjects is determined. The results are subjected to statistical processing, to thereby determine various values (e.g., average and standard deviation). Thus, the reference value (including cutoff value) can be obtained.

The level of the body fluid antibody may be determined by immobilizing the aforementioned body fluid antibody-capturing antigen (including a protein and a peptide), bringing a body fluid sample into contact with the immobilized antigen, and detecting a signal in response to the binding formed by the antigen-antibody reaction between the body fluid antibody-capturing antigen and the antibody (body fluid antibody) against SH3BP5 protein in the body fluid sample. Specifically, the level of the body fluid antibody may be determined through a quantification technique, such as ALPHALISA®, ELISA, indirect immunofluorescence assay, Western blotting (immunoblotting), turbidimetry, nephelometry, latex agglutination turbidimetry, or CLEIA. Any of these techniques is established means for quantifying the level of a target substance (i.e., an antibody in a body fluid sample). For example, ALPHALISA® involves use of glutathione-bound donor beads in the case where the body fluid antibody-capturing antigen is GST-fused SH3BP5 antigen (protein or peptide), or use of streptavidin-bound donor beads in the case where the body fluid antibody-capturing antigen is biotinylated SH3BP5. In ALPHALISA®, the body fluid antibody-capturing antigen, a body fluid sample, and anti-human IgG antibody-bound acceptor beads are mixed together; the mixture is incubated at room temperature for several hours to several days; the resultant antigen-antibody complex is irradiated with light of 680 nm; and emitted light of 520 to 620 nm is detected, to thereby determine the level of the body fluid antibody of interest. In indirect immunofluorescence assay, a body fluid sample is brought into contact with a protein array on which a specific body fluid antibody-capturing antigen is immobilized, and the resultant body fluid antibody-capturing antigen-anti-SH3BP5 body fluid antibody complex is then brought into contact with a fluorescent-labeled secondary antibody, to thereby determine the level of the body fluid antibody against SH3BP5. In ELISA, the secondary antibody used in indirect immunofluorescence assay is labeled with an enzyme for determination of the level of the body fluid antibody. Various enzymes can be used for labeling of the secondary antibody. In Western blotting, a body fluid antibody-capturing antigen is electrophoresed on an SDS-polyacrylamide gel and then transferred from the gel onto a carrier (e.g., nitrocellulose membrane); a body fluid sample is brought into contact with the transferred antigen; and the resultant body fluid antibody-capturing antigen-anti-SH3BP5 body fluid antibody complex is detected by use of a secondary antibody, to thereby determine the level of the body fluid antibody. In turbidimetry or nephelometry, a body fluid sample is brought into contact with a body fluid antibody-capturing antigen, and the resultant body fluid antibody-capturing antigen-anti-SH3BP5 body fluid antibody complex is detected by means of turbidity (turbidimetry) or a change in intensity of scattered light (nephelometry) for determination of the level of the body fluid antibody. In latex agglutination turbidimetry, a body fluid sample is brought into contact with latex particles to which a body fluid antibody-capturing antigen is bound, to thereby form agglutinates of the latex particles through interaction between body fluid antibody molecules bound to the latex particles, and the thus-formed agglutinates are detected for determination of the level of the body fluid antibody. In CLEIA, a body fluid sample is brought into contact with magnetic particles to which a body fluid antibody-capturing antigen is bound, to thereby form a body fluid antibody-capturing antigen-anti-SH3BP5 antibody complex on the magnetic particles; the resultant magnetic particles are collected and unreacted substances are removed; and the complex is detected through, for example, appropriate fluorescence-generating treatment for determination of the level of the body fluid antibody.

(2) The Kit of the Present Invention

The kit of the present invention may include, as components for performing ALPHALISA® as quantification means, for example, a set of GST-fused SH3BP5 antigen (protein or peptide), glutathione-bound donor beads, and acceptor beads, or a set of biotinylated SH3BP5 antigen (protein or peptide), streptavidin-bound donor beads, and acceptor beads.

The kit may include, as components for performing ELISA as quantification means, a plate on which a body fluid antibody-capturing antigen is immobilized, a labeled secondary antibody against a body fluid antibody, and a reagent for visualizing the labeled secondary antibody.

The kit may include, as a component for performing latex agglutination turbidimetry, latex particles to which a body fluid antibody-capturing antigen is bound.

The kit may include, as components for performing CLEIA, magnetic particles to which a body fluid antibody-capturing antigen is bound, a labeled secondary antibody against a body fluid antibody, and a reagent for visualizing the labeled secondary antibody.

The aforementioned components of the kit are merely an example. The kit of the present invention include kits for performing other quantification means. The kit of the present invention may include a smaller number of components than that of the above-exemplified components so as to increase the extent of outsourcing of tests or self-procument. Alternatively, the kit of the present invention may include, for example, a diluent and a reagent tube in addition to the aforementioned components, so that the kit can be readily used as needed. The kit may include additional components corresponding to a specific test.

EXAMPLES

The present invention will next be described by way of examples.

1. Expression and Purification of SH3BP5 Protein

Total RNA was isolated from human U2OS osteosarcoma cells by use of High Pure RNA Isolation Kit (Roche, Basel, Switzerland), and cDNA was synthesized by means of Superscript III First-Strand Synthesis System for RT-PCR (Thermo Fisher Scientific). The resultant cDNA was used as a template, and the full-length cDNA of SH3BP5 was amplified by PCR using Pyrobest DNA polymerase (Takara Bio Inc., Shiga, Japan). The amplified cDNA was inserted into the EcoRI/SalI site of plasmid vector pGEX-4T-1 (GE Healthcare Life Sciences, Pittsburgh, Pa.) having a glutathione S-transferase (GST) gene fragment provided on the upstream side of the cloning site, to thereby prepare pGEX-4T-1-SH3BP5 (i.e., a recombinant plasmid for gene expression), and the nucleotide sequence was determined by means of DNA sequencing. Subsequently, the pGEX-4T-1-SH3BP5 was introduced into *E. coli* BL-21 cells for transformation, and the transformed *E. coli* cells were treated with 0.1 mM IPTG (isopropyl-β-D-thiogalactoside) at 25° C. for four hours, to thereby induce expression of SH3BP5 cDNA. Thereafter, the *E. coli* cells were recovered and lysed by addition of BugBuster Master Mix (Merck Millipore, Darmstadt, Germany), to thereby prepare a protein extract. The GST-SH3BP5 protein contained in the protein extract was purified by means of Glutathione-Sepharose (GE Healthcare Life Sciences) column chromatography. The buffer was exchanged with PBS, and the resultant product was used as SH3BP5 protein antigen. For control, GST was purified in the same manner as described above.

2. Preparation of Peptide Array

The publicly available amino acid sequence (SEQ ID NO: 2) of SH3BP5 protein was searched for its antibody recognition sites by means of the epitope search program ProPred on website (http://www.imtech.res.in/raghava/propred/). As a result, the following five sequences were obtained. For control, the epitope site of C9orf156 (Accession number: NM_001080507) was searched, and the following sequence of the epitope (SEQ ID NO: 8) was obtained.

Six peptides having the following amino acid sequences were each synthesized on a membrane by the Fmoc method using the method by Kato, et al. (Kato R, Kaga C, Kunimatsu M, Kobayashi T, Honda H (2006) Peptide array-based interaction assay of solid-bound peptides and anchorage-dependent cells and its effectiveness in cell adhesive peptide design. J. Biosci. Bioeng. 101: 485-495), to thereby prepare a peptide array.

SH3BP5-43:    FRSVLVEATVKLDE    (SEQ ID NO: 3)

SH3BP5-149:   VHKETAARYNAAMG    (SEQ ID NO: 4)

SH3BP5-161:   MGRMRQLEKKLKRA    (SEQ ID NO: 5)

SH3BP5-185:   KAKYYVQLEQLKKT    (SEQ ID NO: 6)

SH3BP5-327:   EFGMMFPVLGPRSE    (SEQ ID NO: 7)

C9orf156-428: HMTGPVGSLVSLGS    (SEQ ID NO: 8)

The membrane was washed with PBS-T-BSA [phosphate-buffered 1% (w/v) bovine serum albumin, 0.05% Tween-20, 0.05% NaN$_3$] five times. The membrane was allowed to react for 18 hours with a 200-fold diluted serum sample (sample No. HD #1) obtained from a healthy subject who showed no stenosis by carotid artery echography or a 200-fold diluted serum sample (sample No. P #7) obtained from an arteriosclerotic patient who showed stenosis by carotid artery echography. Subsequently, the resultant membrane was washed with PBS-T-BSA 5 times, and then reacted with 10,000-fold diluted FITC-conjugated goat anti-human IgG (Jackson ImmunoResearch, West Grove, Pa.) for 1 hour. The membrane was washed again, and the fluorescence detected using a 488 nm/520 nm filter was quantified by means of Typhoon 9400 Imager (GE Healthcare Life Sciences).

FIG. 1 shows the results of an assay performed on the aforementioned peptide array. Specifically, the membrane having the aforementioned six peptides was reacted with the healthy subject serum sample (sample No. HD #1) and the arteriosclerotic patient serum sample (sample No. P #7), and serum IgG bound to each of the six peptides was detected using a fluorescent-labeled secondary antibody. FIG. 1 is a fluorescent laser scanning image of the results of the detection. The arrow shows a positive spot corresponding to the reaction between the peptide and the patient serum IgG.

As shown in FIG. 1, the peptide "SH3BP5-161" (SEQ ID NO: 5) reacted particularly strongly with the arteriosclerotic patient serum. Thus, the arteriosclerotic patient serum was found to contain the antibody against the peptide; i.e., the antibody against SH3BP5 protein.

3. Analysis by ALPHALISA®

(1) ALPHALISA®

ALPHALISA® (amplified luminescence proximity homogeneous assay) was mainly performed on SH3BP5-161 (SEQ ID NO: 5, unless otherwise specified, "SH3BP5 peptide" described below in the Examples is the peptide having the amino acid sequence of SEQ ID NO: 5); i.e., a body fluid antibody-capturing antigen (in the form of peptide) that most sensitively reacted with anti-SH3BP5 antibody in the serum in the aforementioned test, and on SH3BP5 protein (SEQ ID NO: 2, unless otherwise specified, "SH3BP5 protein" described below in the Examples is the protein having the total amino acid sequence of SEQ ID NO: 2). Specifically, ALPHALISA® was performed by use of a 384-well microtiter plate (white opaque OPTIPLATE™, Perkin Elmer, Waltham, Mass.). Serum 100-fold diluted with an ALPHALISA®-dedicated buffer (25 mM HEPES, pH 7.4, 0.1% casein, 0.5% TRITON™ X-100, 1 mg/mL dextran-500, 0.05% Proclin-300) (2.5 µL) was added to each well and mixed with an antigen; i.e., GST or GST-SH3BP5 protein (10 µg/mL) or biotinylated peptide (bSH3BP5-161) (400 ng/mL) diluted with the ALPHALISA®-dedicated buffer. After incubation at room temperature for 6 to 8 hours, the resultant reaction product was mixed with anti-human IgG-conjugated acceptor beads (2.5 µL at 40 µg/mL) and glutathione- or streptavidin-conjugated donor beads (2.5 µL at 40 µg/mL) diluted with the ALPHALISA®-dedicated buffer. After the mixture had been allowed to stand at room temperature for 1 to 14 days, the resultant photons were counted by means of EnSpire Alpha microplate reader (PerkinElmer), and the number of the photons was defined as "Alpha Count." The level of an antibody specific to SH3BP5 antigen was calculated by subtraction of the value of the control GST (in the case of GST-SH3BP5 protein) or subtraction of the value of the buffer control (in the case of bSH3BP5-161 peptide).

(2) Examination of Diabetes Patients by ALPHALISA®

ALPHALISA® was employed to determine the levels of serum antibodies against GST-SH3BP5 protein and bSH3BP5-161 peptide in diabetes (DM) patients and healthy subjects. DM patient serum samples and healthy subject serum samples were collected in Chiba University Hospital after informed consents had been obtained from all these subjects. The levels of the serum antibodies against GST-SH3BP5 protein and bSH3BP5-161 peptide were significantly higher in the DM patient serum samples than in the healthy subject serum samples (FIG. 2 and Table 1).

Table 1 shows the results of comparison analysis of the levels of SH3BP5 antibodies in the DM patient serum samples and the healthy subject serum samples; i.e., the results of analysis of the data obtained by ALPHALISA® shown in FIG. 2. Table 1 shows (from top to bottom) average, SD, cutoff value (average+2SD), the total number of samples, the number of positive samples exhibiting a cutoff value or higher, and positive rate in the healthy subject serum samples; average, SD, the total number of samples, the number of positive samples exhibiting a cutoff value or higher, and positive rate in the DM patient serum samples; and P value obtained through comparison between the healthy subject serum samples and the DM patient serum samples. P value of 0.05 or less and a positive rate of 10% or more are shown in bold font.

TABLE 1

|    |                 | SH3BP5-GST | bSH3BP5-161 |
|----|-----------------|------------|-------------|
| HD | Average         | 1,850      | 1,387       |
|    | SD              | 955        | 737         |
|    | Cut-off value   | 3,760      | 2,861       |
|    | Total No.       | 81         | 81          |
|    | Positive No.    | 3          | 5           |
|    | Positive rate (%) | 3.7%     | 6.2%        |
| DM | Average         | 3,087      | 2,428       |
|    | SD              | 2,244      | 2,202       |
|    | Total No.       | 275        | 275         |
|    | Positive No.    | 61         | 76          |
|    | Positive rate (%) | 22.2%    | 27.6%       |
|    | P value         | 4.75E−12   | 9.90E−11    |

When the cutoff value was defined as "average+2SD in the healthy subject serum samples," the positive rate was 3.7% in the healthy subject serum samples and 22.2% in the DM patient serum samples (Table 1). The AUC value (areas under the curve) obtained by the ROC (receiver operating curve) analysis was 0.722 in SH3BP5 protein and 0.702 in SH3BP5 peptide. Similarly, the sensitivity and specificity obtained by the ROC analysis were respectively 53.5% and 83.5% in SH3BP5 protein, and were respectively 53.1% and 81.2% in SH3BP5 peptide (FIGS. 2b and 2d). Thus, the results show that the epitope region of SH3BP5-161 peptide reflects the reaction between the entire protein and the serum antibody.

(3) Examination of Transient Ischemic Attack (TIA) Patients and Acute-Stage Cerebral Infarction (aCI) Patients by ALPHALISA®

ALPHALISA® was also employed to determine the levels of serum antibodies against GST-SH3BP5 protein and bSH3BP5-161 peptide in TIA patients and aCI patients. Healthy subject serum samples were obtained from subjects who showed no abnormality by head MRI scan in Port Square Kashiwado Clinic. TIA patient serum samples and aCI patient serum samples were obtained in Chiba Prefectural Sawara Hospital, Chiba Rosai Hospital, Chiba Aoba Municipal Hospital, and Seikei-kai Chiba Medical Center. The results of ALPHALISA® indicated that the levels of antibodies against GST-SH3BP5 protein and bSH3BP5-161 peptide were significantly high in the serum samples from both the TIA and aCI patients (FIGS. 3a and 3b). When the cutoff value was defined as "average+2SD in the healthy subject serum samples," the positive rate of the level of the antibody against SH3BP5 protein was 0.8% in the healthy subjects, 15.6% in the TIA patients, and 15.2% in the aCI patients (Table 2).

Table 2 shows the results of comparison analysis of the levels of SH3BP5 antibodies in the TIA patient serum samples, the aCI patient serum samples, and the healthy subject serum samples; i.e., the results of analysis of the data obtained by ALPHALISA® shown in FIG. 3. The types of numerical values shown in Table 2 are the same as those shown in Table 1.

TABLE 2

|     |                    | SH3BP5-GST | bSH3BP5-161 |
|-----|--------------------|------------|-------------|
| HD  | Average            | 11820      | 2575        |
|     | SD                 | 4,336      | 1,374       |
|     | Av + 2SD (Cut-off) | 20,492     | 5,323       |
|     | Total No.          | 123        | 123         |
|     | Positive No.       | 1          | 6           |
|     | Positive (%)       | 0.8%       | 4.9%        |
| TIA | Average            | 15,188     | 3,641       |
|     | SD                 | 5,693      | 2,217       |
|     | Total No.          | 77         | 77          |
|     | Positive No.       | 12         | 14          |
|     | Positive (%)       | 15.6%      | 18.2%       |
|     | P (P vs HD)        | 0.00002    | 0.00025     |
| aCI | Average            | 14,285     | 3,485       |
|     | SD                 | 5,901      | 2,270       |
|     | Total No.          | 158        | 158         |
|     | Positive No.       | 24         | 25          |
|     | Positive (%)       | 15.2%      | 15.8%       |
|     | P (P vs HD)        | 0.00007    | 0.00004     |

The positive rate of the level of the antibody against SH3BP5 peptide was 4.9% in the healthy subjects, 18.2% in the TIA patients, and 15.8% in the aCI patients. The AUC value of the TIA patients obtained by the ROC analysis was 0.670 in SH3BP5 protein antigen and 0.655 in SH3BP5 peptide antigen (FIGS. 3b and 3e). The AUC value of the aCI patients obtained by the ROC analysis was 0.614 in SH3BP5 protein and 0.620 in SH3BP5 peptide (FIGS. 3c and 3f). Thus, anti-SH3BP5 antibody marker is useful for diagnosis of TIA and aCI.

(4) Examination of Cardiovascular Disease (CVD) Patients and Sleep Apnea Syndrome (OSA) Patients by ALPHALISA®

ALPHALISA® was also employed to determine anti-SH3BP5 antibody levels in sera from patients with CVDs (including acute myocardial infarction and unstable angina). CVD patient serum samples were collected in Chiba University Hospital and Kyoto University Hospital. The levels of the antibodies against both the body fluid antibody-capturing antigens (i.e., SH3BP5 protein and SH3BP5 peptide) were significantly higher in the CVD patient serum samples than in healthy subject serum samples (FIGS. 4a and 4c).

Anti-SH3BP5 antibody levels were determined in sera from patients with sleep apnea syndrome (obstructive sleep apnea (OSA)), since OSA relates to arteriosclerosis and is a high risk factor of CI or CVD. OSA patient serum samples were collected in Chiba University Hospital. The levels of the antibodies against SH3BP5 protein and SH3BP5 peptide were significantly higher in the OSA patient serum samples than in healthy subject serum samples (Table 3).

As described above, Table 3 shows the results of comparison analysis of the levels of SH3BP5 antibodies in the CVD patient serum samples, the OSA patient serum samples, and the healthy subject serum samples. The types of numerical values shown in Table 3 are the same as those shown in Table

TABLE 3

|     |                | SH3BP5-GST | bSH3BP5-161 |
|-----|----------------|------------|-------------|
| HD  | HD Av          | 2,470      | 872         |
|     | HD SD          | 1,316      | 798         |
|     | HD Av + 2SD    | 5,103      | 2,468       |
|     | HD Av + 3SD    | 6,419      | 3,266       |
|     | HD Total No.   | 78         | 78          |
|     | HD Positive No.| 5          | 5           |
|     | HD Positive (%)| 6.4%       | 6.4%        |
| CVD | P Av           | 3,092      | 1,336       |
|     | P SD           | 1,666      | 1,090       |
|     | P Total No.    | 100        | 100         |
|     | P Positive No. | 8          | 13          |
|     | P Positive (%) | 8.0%       | 13.0%       |
|     | P (P vs HD)    | 0.0060     | 0.0013      |

TABLE 3-continued

|   |   | SH3BP5-GST | bSH3BP5-161 |
|---|---|---|---|
| OSA | P Av | 3,124 | 1,335 |
|   | P SD | 2,074 | 1,578 |
|   | P Total No. | 86 | 86 |
|   | P Positive No. | 10 | 11 |
|   | P Positive (%) | 11.6% | 12.8% |
|   | P (P vs HD) | 0.016 | 0.018 |

As shown in Table 3, the positive rate of the level of the antibody against SH3BP5 protein was 6.4% in the healthy subjects, 8.0% in the CVD patients, and 11.6% in the OSA patients. The positive rate of the level of the antibody against SH3BP5 peptide was 6.4% in the healthy subjects, 13.0% in the CVD patients, and 12.8% in the OSA patients.

The AUC value obtained by the ROC analysis was 0.653 in SH3BP5 protein and 0.687 in SH3BP5 peptide (FIGS. 4b and 4d).

These results show that the level of serum anti-SH3BP5 antibody can distinguish a CVD or OSA patient from a healthy subject.

(5) Examination of Chronic Kidney Disease (CKD) Patients by ALPHALISA®

ALPHALISA® was also employed to determine anti-SH3BP5 antibody levels in sera from patients with CKD which relates to arteriosclerosis. CKD patient serum samples were collected from Kumamoto Cohort. CKD was classified into the following three types: type 1: diabetic nephropathy, type 2: nephrosclerosis, and type 3: glomerulonephropathy. Healthy subject serum samples were collected in Chiba University Hospital. The levels of the antibodies against SH3BP5 protein and SH3BP5 peptide were significantly higher in the CKD (all types) patient serum samples than in the healthy subject serum samples (FIGS. 5a and 5e). The positive rate in the case of use of SH3BP5 protein was 2.4% in the healthy subjects, 15.2% in the type 1 CKD patients, 12.5% in the type 2 CKD patients, and 4.1% in the type 3 CKD patients, and the positive rate in the case of use of the peptide antigen was 2.4% in the healthy subjects, 25.5% in the type 1 CKD patients, 28.1% in the type 2 CKD patients, and 13.0% in the type 3 CKD patients (Table 4). The AUC value obtained by the ROC analysis was very high in the case of type 2 CKD; i.e., 0.789 in SH3BP5 protein antigen and 0.839 in the peptide antigen (FIGS. 5c and 5g).

Table 4 shows the results of comparison analysis of the levels of SH3BP5 antibodies in the CKD (type 1, type 2, and type 3) patient serum samples and the healthy subject serum samples. The types of numerical values shown in Table 4 are the same as those shown in Table 1.

TABLE 4

|   |   | SH3BP5-GST | bSH3BP5-161 |
|---|---|---|---|
| HD | HD Av | 1,839 | 1,839 |
|   | HD SD | 1,887 | 902 |
|   | HD Av + 2SD | 5,614 | 3,644 |
|   | HD Total No. | 82 | 82 |
|   | HD Positive No. | 2 | 2 |
|   | HD Positive (%) | 2.4% | 2.4% |
| Type 1 CKD | P Av | 3,467 | 3,011 |
|   | P SD | 3,094 | 1,660 |
|   | P Total No. | 145 | 145 |
|   | P Positive No. | 22 | 37 |
|   | P Positive (%) | 15.2% | 25.5% |
|   | P (P vs HD) | 1.67E-06 | 5.61E-11 |

TABLE 4-continued

|   |   | SH3BP5-GST | bSH3BP5-161 |
|---|---|---|---|
| Type 2 CKD | P Av | 3,392 | 3,052 |
|   | P SD | 2,530 | 1,183 |
|   | P Total No. | 32 | 32 |
|   | P Positive No. | 4 | 9 |
|   | P Positive (%) | 12.5% | 28.1% |
|   | P (P vs HD) | 0.0029 | 0.0000041 |
| Type 3 CKD | P Av | 2,335 | 2,602 |
|   | P SD | 1,692 | 1,347 |
|   | P Total No. | 123 | 123 |
|   | P Positive No. | 5 | 16 |
|   | P Positive (%) | 4.1% | 13.0% |
|   | P (P vs HD) | 0.057 | 0.0000024 |

(6) Examination of Cancer Patients by AlphaLISA (6) Examination of Cancer Patients by ALPHALISA®

ALPHALISA® was also employed to determine anti-SH3BP5 antibody levels in serum samples from patients with esophageal squamous cell carcinoma and colon carcinoma in the same manner as described above, since various body fluid autoantibodies are detected in cancer patients. Patient serum samples were collected in Toho University Hospital. The level of the antibody against SH3BP5 protein was significantly higher in the serum samples from the patients with esophageal squamous cell carcinoma and colon carcinoma than in the healthy subject serum samples, but the positive rate was 10% or less in all the subjects (Table 5). The level of the antibody against SH3BP5 peptide was high in the serum samples from the patients with esophageal squamous cell carcinoma, but the P value was 0.011. No significant difference was observed in the patients with colon carcinoma. The results indicate that the level of the antibody against SH3BP5 peptide antigen (as compared with the antibody against SH3BP5 protein antigen) is a marker corresponding more specifically to arteriosclerotic disease.

Table 5 shows the results of comparison analysis of the levels of SH3BP5 antibodies in the serum samples from the patients with esophageal squamous cell carcinoma (Eso SCC) and colon carcinoma (Colon Ca) and the healthy subject serum samples. The types of numerical values shown in Table 5 are the same as those shown in Table 1.

TABLE 5

|   |   | SH3BP5-GST | bSH3BP5-161 |
|---|---|---|---|
| HD | HD Av | 1,072 | 4,902 |
|   | HD SD | 1,166 | 3,258 |
|   | HD Av + 2SD | 3,405 | 11,419 |
|   | HD Total No. | 64 | 64 |
|   | HD Positive No. | 1 | 3 |
|   | HD Positive (%) | 1.6% | 4.7% |
| Eso SCC | P Av | 1,786 | 6,766 |
|   | P SD | 977 | 4,746 |
|   | P Total No. | 64 | 64 |
|   | P Positive No. | 6 | 7 |
|   | P Positive (%) | 9.4% | 10.9% |
|   | P (P vs HD) | 0.00027 | 0.011 |
| Colon Ca | P Av | 1,653 | 5,928 |
|   | P SD | 1,370 | 3,332 |
|   | P Total No. | 64 | 64 |
|   | P Positive No. | 6 | 4 |
|   | P Positive (%) | 9.4% | 6.3% |
|   | P (P vs HD) | 0.011 | 0.081 |

4. Correlation Analysis

Spearman correlation analysis and multivariate analysis were performed on the level of the serum antibody against SH3BP5 peptide and subject data. The following subject data were used.

Age, gender, body height, body weight, body mass index (BMI), blood pressure, present disease [aCI, TIA, chronic-phase cerebral infarction (cCI), asymptomatic cerebral infarction (asympt CI)], maximum intima-media thickness (max IMT), lifestyle (smoking habit, smoking period, alcohol intake habit, alcohol intake frequency), complication (hypertension, CVD, DM, dyslipidemia), and blood test data [LDL-cholesterol (LDL-C), alkaline phosphatase (ALP), total cholesterol (T-CHO), chlorine (Cl), HDL-cholesterol (HDL-C), potassium (K), creatinine (CRE), gamma-glutamyl transpeptidase (γ-GTP), uric acid (UA), glycated hemoglobin (HbA1c), albumin (ALB), total protein (TP), sodium (Na), alanine aminotransferase (ALT), triglyceride (TG), estimated glomerular filtrating ratio (eGFR), aspartate aminotransferase (AST), cholinesterase (CHE), blood urea nitrogen (BUN), total bilirubin (tBil), blood sugar (BS), lactate dehydrogenase (LDH), and albumin/globulin ratio (A/G)].

The aforementioned correlation analysis was performed on 741 serum samples collected in Chiba Prefectural Sawara Hospital; specifically, healthy subjects: 139 samples, leukomalacia: 79 samples, asympt CI: 15 samples, TIA: 29 samples, aCI: 227 samples, cCI: 58 samples, and disease control group: 194 samples. The results of the multivariate analysis indicated that the level of the antibody against SH3BP5 peptide correlates more strongly with aCI and TIA than with cCI and asympt CI (Table 6). The results of both the Spearman correlation analysis and the multivariate analysis indicated that the level of the antibody against SH3BP5 peptide correlates with max IMT, smoking period, and age. The results of the Spearman correlation analysis indicated that the level of the antibody against SH3BP5 peptide correlates with blood pressure and hypertension of complication. From these results, serum anti-SH3BP5 antibody marker was considered to identify aCI or TIA caused by arteriosclerotic disease resulting from hypertension or smoking habit.

As described above, Table 6 shows the results of correlation analysis of the level of the serum antibody against SH3BP5 peptide antigen and subject data; specifically, the results of the Spearman correlation analysis and the multivariate analysis performed on the 741 serum samples collected in Chiba Prefectural Sawara Hospital. Table 6 (Table 6-1 and Table 6-2) shows the correlation coefficients and P values obtained in these analyses. Significant values of correlation analysis are shown in bold font.

TABLE 6-1

| Subjects' information | | Abbreviation | Spearman r value | Spearman P value | Multivariate r value | Multivariate P value |
|---|---|---|---|---|---|---|
| General | Age | | 0.123 | 0.0016 | 0.123 | 0.0022 |
| | Gender | | −0.020 | 0.6079 | 0.046 | 0.2534 |
| | Body height | Height | −0.070 | 0.0710 | −0.042 | 0.3002 |
| | Body weight | Weight | −0.037 | 0.3361 | 0.030 | 0.4597 |
| | Body mass index | BMI | 0.008 | 0.8336 | −0.027 | 0.4981 |
| | Blood pressure | BP | 0.121 | 0.0023 | 0.043 | 0.2817 |
| Present disease | Acute-phase cerebral infarction | aCI | 0.123 | 0.0015 | −0.247 | 4.3E−10 |
| | Transient ischemic attack | TIA | 0.020 | 0.6062 | −0.070 | 0.0790 |
| | Chronic-phase cerebral infarction | cCI | 0.093 | 0.0170 | −0.077 | 0.0550 |
| | Asymptomatic cerebral infarction | asympt-CI | 0.029 | 0.4505 | −0.047 | 0.2403 |
| Artery stenosis | Maximum intima-media thickness | max IMT | 0.159 | 0.0007 | 0.081 | 0.0443 |
| Life style | Smoking habit (Yes/No) | | 0.092 | 0.0174 | −0.048 | 0.2356 |
| | Smoking period | | 0.135 | 0.0005 | 0.150 | 0.0002 |
| | Alcohol intake habit (Yes/No) | | 0.030 | 0.4346 | 0.019 | 0.6338 |
| | Alcohol intake frequency | | 0.070 | 0.0737 | 0.033 | 0.4054 |
| Blood test | LDL-cholesterol | LDL-C | −0.108 | 0.0449 | | |
| | Alkaline phosphatase | ALP | 0.082 | 0.0458 | 0.070 | 0.0818 |
| | Total cholesterol | T-CHO | −0.068 | 0.1047 | −0.028 | 0.4820 |
| | Chlorine | Cl | 0.056 | 0.1536 | −0.017 | 0.6775 |
| | HDL-cholesterol | HDL-c | −0.053 | 0.2696 | 0.022 | 0.5873 |

TABLE 6-2

| Subjects' information | | Abbreviation | Spearman r value | Spearman P value | Multivariate r value | Multivariate P value |
|---|---|---|---|---|---|---|
| Blood test | Potassium | K | 0.030 | 0.4415 | 0.006 | 0.8854 |
| | Creatinine | CRE | 0.030 | 0.4447 | 0.014 | 0.7266 |
| | Gamma-glutamyl transpeptidase | γ-GTP | 0.030 | 0.4660 | 0.020 | 0.6196 |
| | Uric acid | UA | 0.024 | 0.5948 | 0.054 | 0.1766 |
| | Glycated hemoglobin | HbA1c | 0.023 | 0.6079 | 0.017 | 0.6773 |
| | Albumin | ALB | −0.018 | 0.6444 | 0.062 | 0.1228 |
| | Total Protein | TP | −0.016 | 0.6827 | −0.054 | 0.1761 |
| | Sodium | Na | 0.014 | 0.7159 | 0.042 | 0.2970 |
| | Alanine aminotransferase | ALT (GPT) | 0.012 | 0.7503 | −0.002 | 0.9638 |
| | Triglyceride | TG | 0.013 | 0.7872 | 0.003 | 0.9463 |
| | Estimated glomerular filtrating ratio | eGFR | −0.011 | 0.8026 | 0.004 | 0.9193 |
| | Aspartate aminotransferase | AST (GOT) | 0.008 | 0.8330 | −0.040 | 0.3132 |
| | Cholinesterase | CHE | −0.005 | 0.9054 | −0.025 | 0.5275 |
| | Blood urea nitrogen | BUN | −0.003 | 0.9349 | 0.011 | 0.7897 |
| | Total bilirubin | tBil | −0.002 | 0.9609 | −0.034 | 0.3965 |
| | Blood sugar | BS | −0.001 | 0.9761 | 0.037 | 0.3596 |
| | Lactate dehydrogenase | LDH | 0.000 | 0.9932 | 0.026 | 0.5101 |
| | Albumin/globulin ratio | A/G | 0.000 | 0.9967 | −0.057 | 0.1538 |
| Complication | Hypertension (Yes/No) | HT | 0.130 | 0.0008 | 0.025 | 0.5364 |
| | Cardiovascular disease (Yes/No) | CVD | 0.065 | 0.0958 | 0.067 | 0.0930 |
| | Diabetes mellitus (Yes/No) | DM | 0.026 | 0.4987 | −0.013 | 0.7453 |
| | Dyslipidemia (Yes/No) | | 0.007 | 0.8503 | −0.018 | 0.6500 |

INDUSTRIAL APPLICABILITY

An increase in the level of serum anti-SH3BP5 antibody relates directly to the presence of arteriosclerosis. In addition, the level of serum anti-SH3BP5 antibody increases in sera from patients with various arteriosclerosis-related diseases (e.g., DM, TIA, aCI, CVD, and CKD), and correlates with max IMT or hypertension. Thus, an increase in the level of serum anti-SH3BP5 antibody probably serves as a marker reflecting progression of arteriosclerosis itself. Since this marker correlates with hypertension or smoking habit, a subject who is positive for this marker can probably suppress ongoing arteriosclerosis by reducing the blood pressure or stopping smoking.

Serum samples from aCI or CVD patients were collected within two weeks after the onset of the disease. Since a new autoantibody was less likely to emerge during this period, serum anti-SH3BP5 antibody was probably present before the onset of the disease. Thus, this marker is applicable to prediction of the onset of arteriosclerotic disease. In particular, if prediction of the onset of cerebral infarction or myocardial infarction can lead to prevention of the onset of the disease, this prediction is of social significance. In fact, as described in the Examples, the level of anti-SH3BP5 autoantibody was high in sera from patients with TIA, which is regarded as a previous stage of aCI.

The invention claimed is:

1. A method for detecting anti-SH3BP5 (SRC homology 3 domain binding protein 5) antibody in a subject, said method comprising detecting, in a blood, serum, or plasma sample from a test subject with arteriosclerosis, the amount of anti-SH3BP5 antibody, wherein said anti-SH3BP5 antibody is able to bind to a polypeptide consisting of the amino acid sequence of SEQ ID NO: 2.

2. The method according to claim 1, wherein the sample is a blood sample.

3. The method according to claim 1, wherein the sample is a serum or plasma sample.

4. The method according to claim 1, wherein the amount of anti-SH3BP5 antibody is determined through Enzyme-Linked Immunoassay (ELISA), indirect immunofluorescence assay, Western blotting (immunoblotting), turbidimetry, nephelometry, latex agglutination turbidimetry, or Chemiluminescent Enzyme Immunoassay (CLEIA).

5. The method according to claim 1, wherein said detecting comprises contacting said sample with a polypeptide comprising the amino acid sequence of SEQ ID NO: 2 or 5, and when said sample contains antibody that binds to said polypeptide, binding between the antibody and the polypeptide is detected as a signal.

* * * * *

SEQUENCE LISTING

<160> NUMBER OF SEQ ID NOS: 8

<210> SEQ ID NO 1
<211> LENGTH: 3322
<212> TYPE: DNA
<213> ORGANISM: Homo sapiens

<400> SEQUENCE: 1

| | | | | | |
|---|---|---|---|---|---|
| gcgctgactg | ccgcggcaga | aaggggggcgg | ccgcgcccat | ttcctctgct | ccgccgcggc | 60 |
| cggaggtatc | cgcatcggcg | agctgcgtct | cccgggtgtc | ggccccggcg | gctccccgac | 120 |
| cgtgcccggc | tgtggcgagg | cggctccagc | ccagcctgtg | gcagccgcga | ccccggggc | 180 |
| gctccggagc | ccactgcgcg | gcgcgcgtgc | cggctgcctg | catggacgcg | gcactgaagc | 240 |
| ggagccgctc | ggaggagcca | gccgaaatcc | tgccgcctgc | ccgggacgag | gaggaggagg | 300 |
| aggaagaggg | gatggagcag | gggctggagg | aggaagaaga | ggtggatccc | cggatccagg | 360 |
| gagaactgga | gaagttaaat | cagtccacgg | atgatatcaa | cagacgggag | actgaacttg | 420 |
| aggatgctcg | tcagaagttc | cgctctgttc | tggttgaagc | aacggtgaaa | ctggatgaac | 480 |
| tggtgaagaa | aattggcaaa | gctgtggaag | actccaagcc | ctactgggag | gcacggaggg | 540 |
| tggcgaggca | ggctcagctg | gaagctcaga | aagccacgca | ggacttccag | agggccacag | 600 |
| aggtgctccg | tgccgccaag | gagaccatct | ccctggccga | gcagcggctg | ctggaggatg | 660 |
| acaagcggca | gttcgactcc | gcctggcagg | agatgctgaa | tcacgccact | cagagggtca | 720 |
| tggaggcgga | gcagaccaag | accaggagcg | agctggtgca | taaggagacg | gcagccaggt | 780 |
| acaatgccgc | catgggccgc | atgcgacagc | tggagaagaa | actcaagaga | gccatcaaca | 840 |
| agtccaagcc | ttatttgaa | ctcaaggcaa | agtactatgt | gcagctcgag | caactgaaaa | 900 |
| agactgtgga | tgacctgcag | gccaaactga | ccctggcaaa | aggcgagtac | aagatggccc | 960 |
| tgaagaacct | ggagatgatc | tcagatgaga | tccacgagcg | gcggcgctcc | agtgccatgg | 1020 |
| ggcctcgggg | atgcggtgtt | ggtgctgagg | gcagcagcac | atctgtggag | gatctgccag | 1080 |
| ggagcaaacc | tgagcctgat | gccatttctg | tggcctcgga | ggcctttgaa | gatgacagct | 1140 |
| gtagcaactt | tgtgtctgaa | gatgactcgg | aaacccagtc | cgtgtccagc | tttagttcag | 1200 |
| gaccaacaag | cccgtctgag | atgcctgacc | agttccctgc | ggttgtgagg | cctggcagcc | 1260 |
| tggatctgcc | cagccctgtg | tccctgtcag | agtttgggat | gatgttccca | gtgttgggcc | 1320 |
| ctcgaagtga | atgcagcggg | gcctcctccc | ctgaatgtga | agtagaacga | ggagacaggg | 1380 |
| cagaaggggc | agagaataaa | acaagtgaca | aagccaacaa | caaccggggc | ctcagcagta | 1440 |
| gcagtggcag | tggtggcagc | agtaagagcc | aaagcagcac | ctcccctgag | ggccaggcct | 1500 |
| tggagaaccg | gatgaagcag | ctctccctac | agtgctcaaa | gggaagagat | ggaattattg | 1560 |
| ctgacataaa | aatggtgcag | attggctgat | tcatcctggg | ccctggccga | tgtgcatatc | 1620 |
| aacatttata | catggaactg | gagaacattg | tgccaataat | catttaatat | atgccaaatc | 1680 |

-continued

```
ttacacgtct actctaaact gctctaatga agtttcagtg accttgaggg ctaaagattg   1740
ttcttctggg taagagctct tgggctggtt tttcagagca gagttcttgt tgtgggtaga   1800
ctgtgactag gttcacagcc tttgtggaac attccgtata acggcattgt ggaagcaata   1860
actagttcct atgaaagaac cagagctggg aagatggctg gaagccagg ccaaagtggg    1920
ggcaacagct tgcttctctt tctcttctca ccctcagttt gtatgggaaa atggagatgt   1980
cctctccact ttatcccacg atatctaaat gaaaagaaa gaaacccac acacaaagca     2040
aaaactcaag tattaagagc acatattttt gacccagtgg aggcttaaaa aaaaaaaat    2100
ccaagaacac aattcatttt caccacctct ggtgttcaga gggggctttt aaaaaagcgt   2160
gtatgctggg atacccatta aaaccatttt ctagaaggct accatgagct gcactttttg   2220
gggtgggaaa ggtgaatgcc agtggggatg cgggggatg agggtaggag ggacttatag    2280
aagggggattt gtggctgtgg gggagaaggt tctacagcat aagccttatc ctgccagcca  2340
aggggattta ttctaagaga agtgcatgtg aagaatggtt gccactgtta ttagattgac   2400
aagatgttaa tttctctgta ggttgtaact ttaaaaataa atgaaattat ttaagggtta   2460
tgctgcacta gtattcctta gaggaaacag ttctttaaag ttaggaaagg gagtaggcag   2520
gcatgtgttg gcaaaggctg ttaatagtag ttaagtgtta agactgcttt tctttaacgt   2580
tttcatggta atgcatattt agagcactgt attttgtct tgttaagaaa atttagcatt    2640
tctaaaagaa aaaagcaacc ctcttcaaa ctgttaattc tgtcacagcc tgtatatttt    2700
agtcatttgt aaatctcttc atacaatagt gacttctttt ttgactgata cagtatctta   2760
attacaaggt tattttgtac ttgtcttaat acactaagtg taataaaaac ggcttgagaa   2820
aagtttctcc tttctgtgac ttcaaataag aactcccagt attgcctaaa tcttctaggc   2880
aacccttttt ccataaggaa gagcatggag tgctgtggtc accagtaatc attttcaatt   2940
aattaaggtc atgaacagta ataatttaag ccttgtttac caaggttttga attctacttt   3000
tgctgttgct aaagctgtgg gcaatgagga gacacagtgg cagataaaga cgaggtggtg   3060
acgctggagg agtgggcctc ggctgcacac tgcagtctcg aagcttaagt gttgctgtca   3120
gtcagttctc atcccagag aattatttaa ttaattaact gggggggta cactgggca    3180
ttagactttt aaaagctccc cgagggaatt caaatgtgca ttcagagttg agaatcagat   3240
ggattctttc ttttgtggaa atgtttata atattggact cttaatccgc atttcattat    3300
taaagcatgc tgtggagaaa aa                                            3322
```

<210> SEQ ID NO 2
<211> LENGTH: 455
<212> TYPE: PRT
<213> ORGANISM: Homo sapiens

<400> SEQUENCE: 2

```
Met Asp Ala Ala Leu Lys Arg Ser Arg Ser Glu Glu Pro Ala Glu Ile
1               5                   10                  15

Leu Pro Pro Ala Arg Asp Glu Glu Glu Glu Glu Glu Gly Met Glu
                20                  25                  30

Gln Gly Leu Glu Glu Glu Glu Val Asp Pro Arg Ile Gln Gly Glu
            35                  40                  45

Leu Glu Lys Leu Asn Gln Ser Thr Asp Asp Ile Asn Arg Arg Glu Thr
        50                  55                  60

Glu Leu Glu Asp Ala Arg Gln Lys Phe Arg Ser Val Leu Val Glu Ala
65                  70                  75                  80
```

```
Thr Val Lys Leu Asp Glu Leu Val Lys Lys Ile Gly Lys Ala Val Glu
             85                  90                  95
Asp Ser Lys Pro Tyr Trp Glu Ala Arg Val Ala Arg Gln Ala Gln
            100                 105                 110
Leu Glu Ala Gln Lys Ala Thr Gln Asp Phe Gln Arg Ala Thr Glu Val
            115                 120                 125
Leu Arg Ala Ala Lys Glu Thr Ile Ser Leu Ala Glu Gln Arg Leu Leu
            130                 135                 140
Glu Asp Asp Lys Arg Gln Phe Asp Ser Ala Trp Gln Glu Met Leu Asn
145                 150                 155                 160
His Ala Thr Gln Arg Val Met Glu Ala Glu Gln Thr Lys Thr Arg Ser
                165                 170                 175
Glu Leu Val His Lys Glu Thr Ala Ala Arg Tyr Asn Ala Ala Met Gly
            180                 185                 190
Arg Met Arg Gln Leu Glu Lys Lys Leu Lys Arg Ala Ile Asn Lys Ser
            195                 200                 205
Lys Pro Tyr Phe Glu Leu Lys Ala Lys Tyr Tyr Val Gln Leu Glu Gln
            210                 215                 220
Leu Lys Lys Thr Val Asp Asp Leu Gln Ala Lys Leu Thr Leu Ala Lys
225                 230                 235                 240
Gly Glu Tyr Lys Met Ala Leu Lys Asn Leu Glu Met Ile Ser Asp Glu
                245                 250                 255
Ile His Glu Arg Arg Ser Ser Ala Met Gly Pro Arg Gly Cys Gly
            260                 265                 270
Val Gly Ala Glu Gly Ser Ser Thr Ser Val Glu Asp Leu Pro Gly Ser
            275                 280                 285
Lys Pro Glu Pro Asp Ala Ile Ser Val Ala Ser Glu Ala Phe Glu Asp
            290                 295                 300
Asp Ser Cys Ser Asn Phe Val Ser Glu Asp Ser Glu Thr Gln Ser
305                 310                 315                 320
Val Ser Ser Phe Ser Ser Gly Pro Thr Ser Pro Ser Glu Met Pro Asp
                325                 330                 335
Gln Phe Pro Ala Val Val Arg Pro Gly Ser Leu Asp Leu Pro Ser Pro
            340                 345                 350
Val Ser Leu Ser Glu Phe Gly Met Met Phe Pro Val Leu Gly Pro Arg
            355                 360                 365
Ser Glu Cys Ser Gly Ala Ser Ser Pro Glu Cys Glu Val Glu Arg Gly
            370                 375                 380
Asp Arg Ala Glu Gly Ala Glu Asn Lys Thr Ser Asp Lys Ala Asn Asn
385                 390                 395                 400
Asn Arg Gly Leu Ser Ser Ser Gly Ser Gly Gly Ser Ser Lys Ser
            405                 410                 415
Gln Ser Ser Thr Ser Pro Glu Gly Gln Ala Leu Glu Asn Arg Met Lys
            420                 425                 430
Gln Leu Ser Leu Gln Cys Ser Lys Gly Arg Asp Gly Ile Ile Ala Asp
            435                 440                 445
Ile Lys Met Val Gln Ile Gly
    450                 455

<210> SEQ ID NO 3
<211> LENGTH: 14
<212> TYPE: PRT
<213> ORGANISM: Homo sapiens

<400> SEQUENCE: 3
```

```
Phe Arg Ser Val Leu Val Glu Ala Thr Val Lys Leu Asp Glu
1               5                   10

<210> SEQ ID NO 4
<211> LENGTH: 14
<212> TYPE: PRT
<213> ORGANISM: Homo sapiens

<400> SEQUENCE: 4

Val His Lys Glu Thr Ala Ala Arg Tyr Asn Ala Ala Met Gly
1               5                   10

<210> SEQ ID NO 5
<211> LENGTH: 14
<212> TYPE: PRT
<213> ORGANISM: Homo sapiens

<400> SEQUENCE: 5

Met Gly Arg Met Arg Gln Leu Glu Lys Lys Leu Lys Arg Ala
1               5                   10

<210> SEQ ID NO 6
<211> LENGTH: 14
<212> TYPE: PRT
<213> ORGANISM: Homo sapiens

<400> SEQUENCE: 6

Lys Ala Lys Tyr Tyr Val Gln Leu Glu Gln Leu Lys Lys Thr
1               5                   10

<210> SEQ ID NO 7
<211> LENGTH: 14
<212> TYPE: PRT
<213> ORGANISM: Homo sapiens

<400> SEQUENCE: 7

Glu Phe Gly Met Met Phe Pro Val Leu Gly Pro Arg Ser Glu
1               5                   10

<210> SEQ ID NO 8
<211> LENGTH: 14
<212> TYPE: PRT
<213> ORGANISM: Homo sapiens

<400> SEQUENCE: 8

His Met Thr Gly Pro Val Gly Ser Leu Val Ser Leu Gly Ser
1               5                   10
```